US008383870B2

(12) United States Patent
Knight et al.

(10) Patent No.: US 8,383,870 B2
(45) Date of Patent: Feb. 26, 2013

(54) ENVIRONMENTALLY FRIENDLY METHODS AND SYSTEMS OF ENERGY PRODUCTION

(75) Inventors: Roy C. Knight, Germantown, TN (US); Rolf L. Onjukka, Cordova, TN (US); Patrick J. Doyle, Walls, MS (US)

(73) Assignee: Federal Express Corporation, Memphis, TN (US)

( * ) Notice: Subject to any disclaimer, the term of this patent is extended or adjusted under 35 U.S.C. 154(b) by 986 days.

(21) Appl. No.: 12/379,249

(22) Filed: Feb. 17, 2009

(65) Prior Publication Data

US 2010/0011778 A1 Jan. 21, 2010

Related U.S. Application Data

(60) Provisional application No. 61/129,787, filed on Jul. 18, 2008.

(51) Int. Cl.
*C07C 1/00* (2006.01)
*F02C 1/00* (2006.01)
(52) U.S. Cl. .......... 585/240; 585/242; 48/197 R; 60/772
(58) Field of Classification Search ............... 585/240, 585/242; 201/25; 48/197 R; 60/772
See application file for complete search history.

(56) References Cited

U.S. PATENT DOCUMENTS

| | | | | |
|---|---|---|---|---|
| 5,659,977 A | * | 8/1997 | Jensen et al. | 34/547 |
| 7,191,736 B2 | * | 3/2007 | Goldman | 123/1 A |
| 7,556,736 B2 | * | 7/2009 | Price et al. | 210/603 |
| 7,578,927 B2 | * | 8/2009 | Marker et al. | 208/67 |
| 7,621,129 B2 | * | 11/2009 | DuBois | 60/641.2 |
| 7,816,570 B2 | * | 10/2010 | Roberts et al. | 585/240 |
| 7,838,272 B2 | * | 11/2010 | Miller | 435/167 |
| 7,888,540 B2 | * | 2/2011 | Deluga et al. | 585/14 |
| 8,153,850 B2 | * | 4/2012 | Hall et al. | 585/240 |
| 2006/0266039 A1 | | 11/2006 | Skowronski et al. | |
| 2008/0166265 A1 | * | 7/2008 | Day | 422/30 |

FOREIGN PATENT DOCUMENTS

| | | |
|---|---|---|
| DE | 20 2005 010 265 U1 | 8/2006 |
| DE | 10 2007 014 631 A1 | 9/2008 |
| EP | 2 058 515 A1 | 5/2009 |
| EP | 2105495 * | 9/2009 |
| WO | WO 2006/019900 A1 | 2/2006 |
| WO | WO 2007/144103 A1 | 12/2007 |

OTHER PUBLICATIONS

International search report issued on related PCT (PCT/US2009/003948), dated Feb. 24, 2011.
Written Opinion issued on related PCT (PCT/US2009/003948), dated Feb. 24, 2011.

* cited by examiner

*Primary Examiner* — Nina Bhat
(74) *Attorney, Agent, or Firm* — Finnegan, Henderson, Farabow, Garrett & Dunner, LLP

(57) ABSTRACT

A process of energy production is disclosed. The process includes integrating three or more energy production technologies such that a first byproduct of a first energy production technology is applied to a second energy production technology and a second byproduct of the second energy production technology is applied to a third energy production technology. The process also includes operating the integrated energy production technologies to produce energy such that at least a portion of the first byproduct is utilized in an operation of the second energy production technology and a portion of the second byproduct is utilized in an operation of the third energy production technology.

34 Claims, 16 Drawing Sheets

ENVIRONMENTALLY FRIENDLY METHODS AND SYSTEMS OF ENERGY PRODUCTION

This application claims the benefit of U.S. Provisional Patent Application Ser. No. 61/129,787, filed Jul. 18, 2008.

TECHNICAL FIELD

This disclosure relates generally to environmentally friendly methods and systems of energy production and, more particularly, to a synergistic method of producing energy by combining certain energy production technologies together to reduce the effects of energy production on the environment.

BACKGROUND

Modern civilization is heavily dependent on carbonaceous materials for producing energy. These carbonaceous materials include hydrocarbon based fuels used in combustion engines and coal and other fuels used in electrical power generation. Due to the recent increase in demand for fuel from emerging countries such as India and China, and the limited production of crude oil, there has been a substantial increase in the price of liquid fuel. In order to increase production of liquid fuel, low cost alternative means of production are needed to meet the ever increasing demand. Many countries have vast amount of available carbonaceous feedstock that can be used for electricity production and for the production of fuels (collectively referred to herein as energy production). One of the more common carbonaceous feedstock is coal, which is often used for power generation. However, the use of such feedstocks in conventional energy production techniques can adversely affect the environment.

One of the most abundant carbonaceous feedstocks found in the United States is coal. By some estimates, the amount of coal in the U.S. is projected to last between 250-300 years at current rates of consumption. The combustion of coal produces over half of the electricity generated in the U.S. When used for electricity generation, coal is usually pulverized and burned in a furnace with a boiler. The furnace heat converts the boiler water to steam, which is then used to spin turbines that turn generators to create electricity. Coal can also be converted to a gaseous fuel by a process commonly referred to as coal gasification. In coal gasification, molecules of coal are broken into smaller molecular weight molecules, usually by subjecting it to high temperature and pressure, using steam and measured amounts of oxygen. This process leads to the production of a gaseous fuel, referred to as synthetic gas or syngas. Syngas is a mixture mainly consisting of carbon monoxide (CO) and hydrogen ($H_2$) and may be used as a fuel. Coal can also be liquefied into liquid fuels (such as, gasoline, diesel, etc.) by several different well known processes such as, for example, the Fischer-Tropsch process, the Bergius process, the Karrick process, and others. In some of these processes, syngas or slurry is subjected to different conditions of temperature and pressure in the presence of a catalyst to produce different types of liquid fuels.

When coal is burned for electricity production, gasified to produce gaseous fuel, or liquefied to produce liquid fuel, it releases into the atmosphere green house gases (GHG) such as carbon dioxide ($CO_2$) and other harmful pollutants such as oxides of sulfur ($SO_x$) and oxides of nitrogen ($NO_x$). As concerns of global warming intensify, there is increased pressure to reduce the amount of GHGs released into the atmosphere. One suggested method to reduce the GHGs released into the atmosphere is by sequestering the gaseous emissions in underground storage facilities. However, underground storage of $CO_2$ and other emissions would increase costs and raise concerns about possible leakage from underground rock formations or possible contamination of water supplies.

The present disclosure is directed at improved methods and systems of producing energy and fuel while overcoming the shortcomings discussed above and/or other shortcomings in existing technology.

SUMMARY OF THE DISCLOSURE

In one aspect, the present disclosure is directed to a process of energy production. The process includes integrating three or more energy production technologies such that a first byproduct of a first energy production technology is applied to a second energy production technology and a second byproduct of the second energy production technology is applied to a third energy production technology. The process also includes operating the integrated energy production technologies to produce energy such that at least a portion of the first byproduct is utilized in an operation of the second energy production technology and a portion of the second byproduct is utilized in an operation of the third energy production technology.

In another aspect, the present disclosure is directed to a process for producing energy. The process includes integrating a power generation facility, a carbonaceous feedstock gasification facility, and a bioreactor facility to produce electric power, liquid fuel, and biomass. The process also includes utilizing a byproduct of one or more of the said facilities to assist in the production of one or more of the electric power, the liquid fuel, and the biomass.

In yet another aspect, the present disclosure is directed to a method of energy production. The method includes producing a first energy and first byproducts in a first energy production technology and utilizing at least a portion of the first byproducts to produce a second energy and second byproducts in a second energy production technology. The method also includes utilizing at least a portion of the third byproducts to produce a third energy and third byproducts in a third energy production technology. The first byproducts, the second byproducts, and the third byproducts include at least one of $CO_2$, an oxide of sulfur, and an oxide of nitrogen. Utilizing the first byproducts and utilizing the second byproducts reduces a concentration of at least one of the $CO_2$, the oxide of sulfur, or the oxide of nitrogen released to atmosphere as compared to a case where the first byproducts and second byproducts are not so utilized.

In a further aspect, the present disclosure is directed to a method of energy production. The method includes operating an integrated energy production facility, the integrated energy production facility including at least three individual energy production facilities fluidly coupled with each other. Each of the individual energy production facilities produces energy and emits byproducts that include at least one of $CO_2$, an oxide of sulfur, and an oxide of nitrogen, wherein operating the integrated energy production facility includes utilizing at least a portion of the byproducts to produce the energy. The method also includes releasing a portion of the byproducts to atmosphere, a concentration of at least one of the $CO_2$, the oxide of sulfur, and the oxide of nitrogen being lower in the released portion than in a case where the individual energy production facilities are not integrated.

BRIEF DESCRIPTION OF THE DRAWINGS

The accompanying drawings, which are incorporated in and constitute a part of this specification, illustrate embodiments of the disclosure.

DETAILED DESCRIPTION

Reference will now be made to exemplary embodiments of the disclosure, examples of which are illustrated in the accompanying drawings. Wherever possible, the same reference numbers will be used throughout the drawings to refer to the same or like parts.

Figure 1:
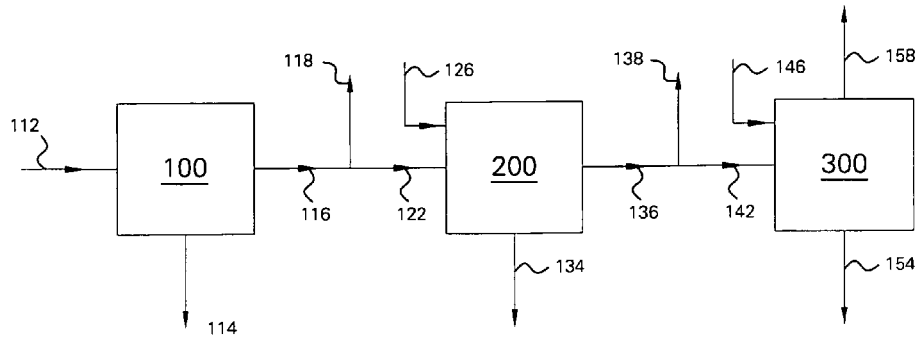
FIG. 1 is a schematic illustration of an exemplary environmentally friendly method of energy production using three integrated energy production technologies (EPTs)

FIG. 1 illustrates a schematic of an exemplary environmentally friendly method of energy production. In general, energy production technologies (EPTs) 100, 200, and 300 may be any known technology to produce energy, as well as future technologies that can be used as part of the disclosure. The energy produced by the energy production technologies may include electric power, or any type of fuel (solid, liquid, and gaseous) that may be used to produce energy and do work (such, as gasoline, jet fuel, LPG, propane, etc.). Non-limiting examples of EPTs 100, 200, and 300 may include coal power plants, coal gasification plants, coal to liquid (CTL) facilities, oil refineries, nuclear power plants, bioreactors, garbage incineration power generation facilities, plasma incineration power generation facilities, and cavitation processing facilities.

Input 112 may be directed into EPT 100 to produce energy 114. In the process of producing energy from input 112, EPT 100 may also release byproducts 116. These byproducts may include emissions (such as $CO_2$, $NO_x$, $SO_x$, etc.) and solid or liquid material that may be produced in the process of EPT 100. Byproducts 116 may include oxides of sulfur and oxides of nitrogen. For example, in an embodiment where EPT 100 is a coal power plant that produces electricity by burning coal, input 112 may include coal and water that are directed into the furnace and the boiler, respectively, of the coal power plant. The coal may be burned in the furnace to produce steam in the boilers. This steam may drive one or more turbines coupled to an electric generator to produce electric power. In this example, the electricity produced by these generators would be energy 114. The waste heat and steam released into the atmosphere, the flue gases, and the solid ash produced due to the combustion of coal, would constitute the byproducts 116 of the coal power plant.

A portion 118 of these byproducts 116 may be separated as waste solids and emissions, while the remainder 122 may be directed into EPT 200, into EPT 300, or both. Parts of the separated portion 118 of the byproducts may be used in other processes or may be discarded into the atmosphere. Although not expressly illustrated in FIG. 1, a portion of byproducts 116 may also be recirculated back into EPT 100. In the embodiment of the coal power plant, the separated portion 118 may include ash and other solid waste produced due to the combustion of coal, and the remaining portion 122 directed into EPT 200 may include a portion or all of flue gases and the waste heat and steam produced by the coal power plant. A portion of the waste steam and heat may be reused in the coal power plant to increase the efficiency or minimize the energy consumed the coal power plant. In this case, the reused portion may form the recirculated part of the byproducts 116. In other embodiments of the present disclosure, a part of the ash of separated portion 118 may be recycled and used to produce building materials and other such products.

In general, any portion of the byproducts produced by EPT 100 may be directed into EPT 200 or EPT 300 as long as the resulting combination either increases efficiency of energy production or reduces the release of harmful byproducts to the environment, preferably both. Preferably, the percentage of the byproducts directed to a different EPT are optimized to achieve the goals of the user. These goals and the optimization will depend on a variety of factors including, the specific characteristics of the EPTs, the commercial costs of alternative sources of energy, governmental regulations, and environmental concerns. In some embodiments substantially all of the byproducts 116 may be directed to another EPT, such as EPT 200.

In addition to the byproducts supplied to EPT 200 from EPT 100 (remainder 122), input 126 may also be directed into EPT 200 to produce energy 134. In addition to energy 134, byproducts 136 may also be produced by EPT 200. A portion 138 of these byproducts 136 may be separated, and the remainder 142 may be directed into EPT 300, or to EPT 100. A part of the separated portion 138 may be used to produce other products and another part may be discarded. As with byproducts 116 of EPT 100, a portion of byproducts 136 may also be recirculated and used in EPT 200 (not illustrated in FIG. 1).

In addition to remainder 142, input 146 may also be directed into EPT 300. EPT 300 may use input 146 and remainder 142 to produce energy 154 and create byproducts 158. As in the case with byproducts 116 and 136, portions of by-product 158 may be captured to produce other products, recirculated back to EPT 300, discarded, or directed into other energy producing technologies. It should be emphasized that, although only three EPTs are illustrated in FIG. 1, embodiments of the present disclosure may include any number of EPTs coupled together, or otherwise integrated, to use at least some portion of byproducts created by another EPT to produce energy.

As mentioned earlier, energy 114, 134, and 154 may be of a form that may be directly used to produce mechanical work, or may be a fuel source that may be combusted (or used in another manner) to produce work. For instance, in an embodiment where EPT 100 is a coal power plant and EPTs 200 and 300 are a coal to liquid (CTL) facility and a bioreactor, respectively, energy 114 produced by EPT 100 may be electric power, energy 134 produced by EPT 200 may include various liquid and gaseous forms of fuels, and energy 154 produced by EPT 300 may include food stock and/or different forms of fuels. In a case where the produced energy is a food source, this food source may be consumed by humans or animals to create energy and do work, and in a case where the produced energy is a fuel, this fuel may be combusted (or otherwise processed) in a subsequent process to do work.

Although FIG. 1 illustrates EPTs 100, 200, and 300 coupled together in a serial manner, other configurations of integration are also contemplated. For instance, portions of byproducts 116, 136, and 158 from EPTs 100, 200, and 300 may be directed into any or all of EPTs 100, 200 and 300. As a result of the integration of EPTs, and utilization of portions of byproducts produced by one EPT in the process of another EPT, some of the constituents of the byproducts released into the atmosphere (or otherwise discarded) may be reduced. For instance, by the integration of EPTs 100, 200, and 300, the sum total of the green house gas $CO_2$ released into the atmosphere is preferably lower than the amount of $CO_2$ that would be released if EPTs 100, 200, and 300 were operated independently (that is, not integrated). Similarly, the total sum of input required to operate the systems may be reduced, by applying energy sources from one system to feed another. For instance, excess heat and/or pressure generated in system 100 (e.g., a coal power plant 100) may be applied to system 200 (e.g., a coal to liquid fuel system 200), thereby reducing the energy input otherwise needed to operate system 200. When system 300 includes a bioreactor, part of the energy applied may be solar energy, thereby using a readily available and free source of energy. In addition, when system 300 includes a bioreactor, byproducts (such as CO2, oxides of sulfur, and oxides of nitrogen) from one or both of systems 100 and 200 can be applied to the bioreactor.

The following paragraphs describe some exemplary embodiments of the disclosed environmentally friendly methods of energy production. These embodiments are only used to better describe and highlight various aspects of the disclosure, and not intended as an exhaustive list of potential embodiments.

Figure 2:
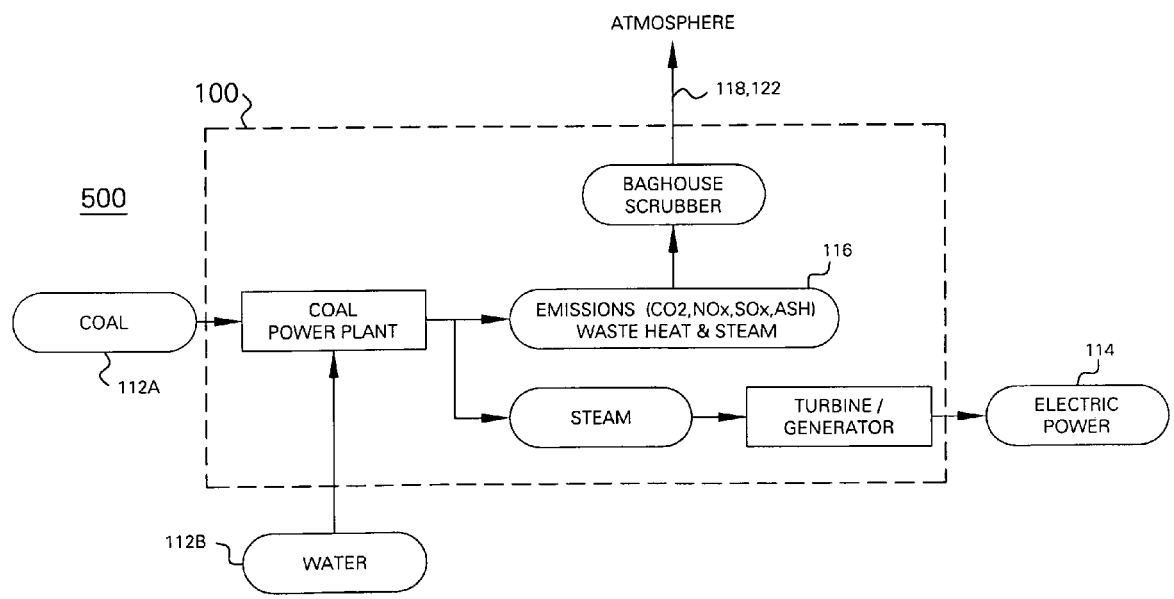
FIG. 2 is a schematic illustration of an exemplary EPT that can be used as one of the integrated technologies of FIG. 1.

EPT 100 may be a coal power plant that produces electricity by using the heat of combustion of coal to produce power. FIG. 2 is a schematic that illustrates the operation of EPT 100. EPT 100 may be built in an area 500 that is permitted for industrial use and, in some instances, located away from highly populated areas. Area 500 may have an abundant supply of coal and water, and an infrastructure configured to deliver the coal and water as input (112A and 112B) to EPT 100. This infrastructure may include pulverizers and other equipment configured to reduce the coal to a form suited for EPT 100, and access to rail and other transportation systems that deliver personnel and raw materials to area 500. Area 500 may also have access to large areas of unused land that separate EPT 100 from surrounding communities.

Since operation of coal power plants are well known in the art, the operation of EPT 100 is not described in detail herein. In general, EPT 100 may combust the coal input 112A in a furnace to boil water (input 112B) in a boiler to create steam. This steam may be used to spin a turbine coupled to a generator that produces electric power. This electric power may be used to supply an electric grid coupled thereto. In some cases, the electric power generated by EPT 100 may not be constant, but may vary over time depending upon the need. For instance, power generation by EPT 100 may be higher at times of peak consumption in the electric grid and lower at times of reduced consumption. In some such cases, it may be more economical to operate the furnace and the boiler at a higher rate, and even constant rate, and bypass some of the steam from the turbine during times of reduced need. In these cases, not all the steam produced by the boiler may be used to spin the turbine, and some steam (and heat) may be bypassed or wasted. In the application of the present disclosure, such unused stream (and heat) is applied to other EPTs, thereby conserving energy and improving operating efficiency.

After spinning the turbine, the steam may be condensed into water in a condenser, and recirculated in a closed loop back to the boiler. EPT 100 may also include circulating cooling water system that may be used to condense the steam in the condenser. This cooling water system may circulate cool water from a water source (such as a stream, river, lake, or another similar body of water) on area 500 through the condenser and exhaust warmer water back into the water source. The combustion of coal in the furnace may produce combustion products such as $CO_2$, $NO_x$, $SO_x$, and residual ash or slag. These combustion products along with the steam and heat that is wasted in EPT 100 may form the byproducts 116 of EPT 100. Some of these byproducts (such as $CO_2$, $NO_x$ and $SO_x$) may be harmful for the environment and may be regulated by various governments. The emission of these harmful constituents may also make it politically difficult to successfully gain the governmental or public approval necessary to build new plants. To reduce the concentration of these regulated species in byproducts 116, processes such as containment and/or scrubbing may be employed as part of EPT 100. The byproducts 116 may then be released into the atmosphere.

Figure 3:
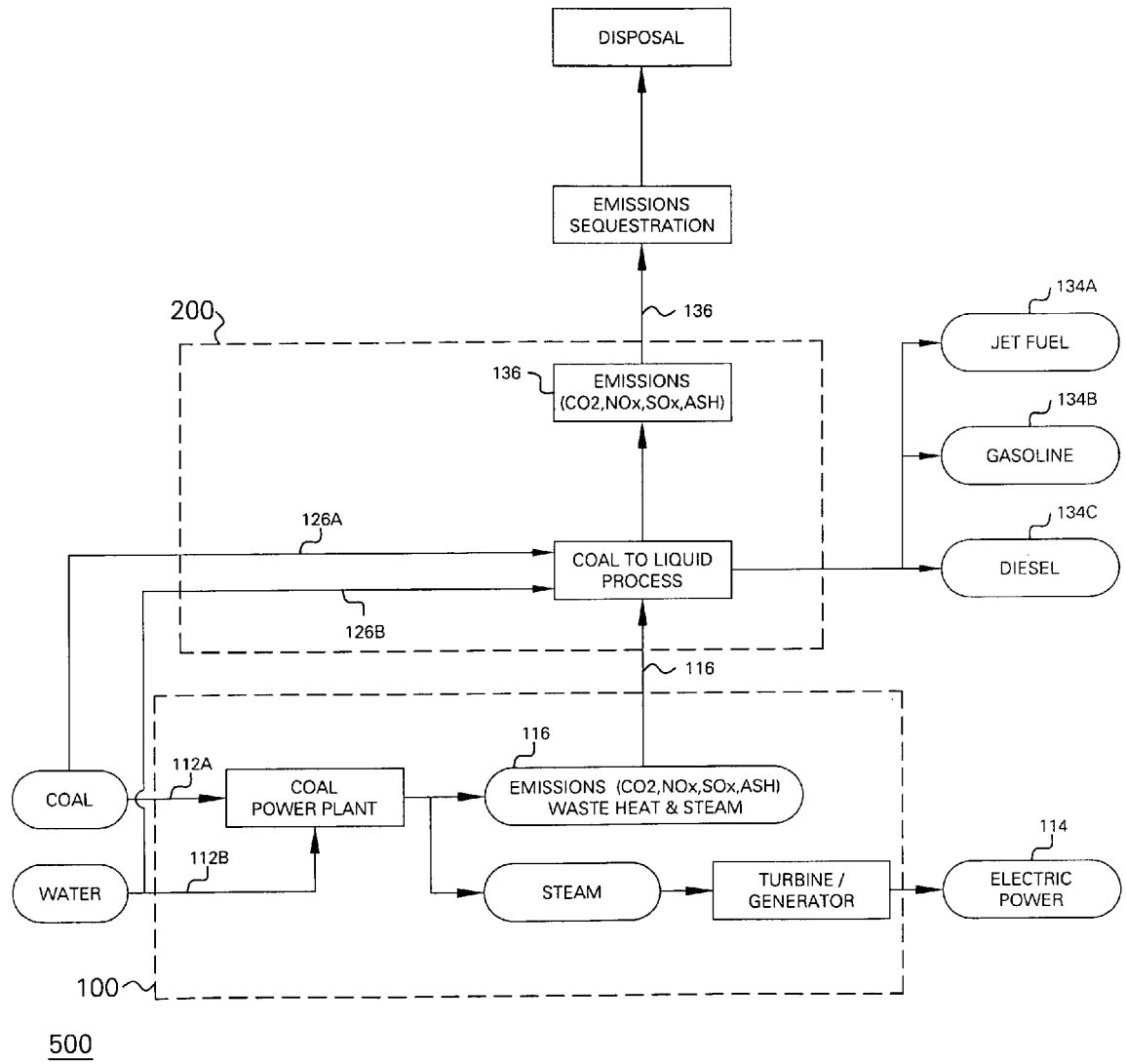
FIG. 3 is a schematic illustration that shows another exemplary EPT that can be used as one of the integrated technologies of FIG. 1, integrated with the EPT of FIG. 2.

FIG. 3 illustrates a schematic of EPT 200 that may be coupled to the coal power plant in area 500. EPT 200 may be a CTL plant that liquefies coal using indirect gasification or direct solvent extraction to produce different types of fuel oils, typically called synthetic fuels. Since the operation of both direct (such as those following the Bergius process) and indirect (such as those following the Fischer-Tropsch process) CTL facilities to produce synthetic fuels from coal are well known in the art, a detailed description of these processes are not provided herein. Details of the CTL process that may be affected by the integration of EPTs 100 and 200 are described herein. EPT 200 may be located in area 500 to utilize the established infrastructure and logistic support of EPT 100. The large amount of free space in area 500 and the preexisting supply of coal and water in area 500 may reduce the cost of implementation of EPT 200. Additionally, use of existing infrastructure (such as, coal and water delivery systems, etc.) and land for EPT 200 may ease securing of the required governmental approvals and reduce public resistance to the development of a CTL facility. In one embodiment, EPT 100 and EPT 200 are located in close proximity to each other, and to sources of coal and water.

Coal and water may be directed into EPT 200 as inputs 126A, 126B. By locating EPT 200 in area 500, the source of inputs 112A of EPT 100 and 126A of EPT 200 may be the same, and the source of inputs 112B of EPT 100 and 126B of EPT 200 may be the same. Byproducts 116 of EPT 100 may also be directed into EPT 200. In some embodiments, as discussed with reference to FIG. 1, only a portion (for example, portion 122 in FIG. 1) of byproducts 116 may be directed into EPT 200.

Within EPT 200, the coal inputted (input 126A) into EPT 200 may be converted into a mixture of carbon monoxide and hydrogen (known as "syngas") following known coal to liquid processes. This conversion process involves a reaction between coal and a controlled amount of steam at high temperatures. In accordance with the present disclosure, this reaction may use the waste heat and steam from EPT 100, as part of the energy required, to convert the coal to syngas. The moisture content in byproducts 116 may also be converted into its constituent hydrogen and oxygen in EPT 200. In some embodiments, the amount of syngas produced by EPT 200 may be further increased by applying some or all of the $CO_2$ in byproducts 116 from EPT 100 as an additional input to EPT 200. This $CO_2$ may be reduced to carbon monoxide by known processes such as the reverse water gas shift reaction or by using amine based solvents. Some examples of processes that may be used to convert $CO_2$ contained in byproducts 116 to hydrocarbons are described in U.S. Patent Publication 2007/0244208 to Shulenberger et al. and WIPO publication WO/2006/006164. These publications are incorporated by reference herein.

For indirect CTL, the syngas produced may be converted into hydrocarbon fuels and other chemical products by known processes, such as the Fischer-Tropsch (FT) process. In this process, the syngas produced by the gasification of coal (and reduction of $CO_2$ in by-product 116) may be subjected to a high temperature and pressure in the presence of a metallic catalyst. Depending upon the temperature, pressure and the catalyst used, the syngas may be converted into liquid hydrocarbons of various forms, such as, for example, jet fuel 134A, gasoline 134B, and diesel 134C. The production of the liquid fuels using the CTL process also produces $CO_2$ and other harmful pollution gases such as $NO_x$ and $SO_x$. In some embodiments, a portion of the byproducts 136 produced by EPT 200 may be recirculated back into EPT 200, or may also be used for electrical power generation. In addition, the electrical power produced by EPT 100 may provide the power for various systems of EPT 200, resulting in a reduction of power consumption. Excess electrical power may also be transferred to the power grid. At least a portion of the byproducts 136 may be applied to EPT 300, as described more fully below.

Utilizing byproducts 116 of EPT 100 in the process of EPT 200 may make the energy generation process of EPT 200 more efficient, by reducing the need for burning coal to generate the heat and steam used in the process. As described earlier, in some embodiments of the present disclosure, EPT 200 may also be configured to convert a portion of the $CO_2$ in byproducts 116 and 136 to hydrocarbon based fuels. In this case, the efficiency of the EPT 200 may be further improved due to the conversion of waste $CO_2$ to useful fuel. Additionally, utilizing the infrastructure and logistical support of an existing coal power plant (EPT 100) for a CTL plant (EPT 200) may reduce the cost of implementation of the CTL plant and reduce the resources that may have to expended to secure the necessary government approvals. Furthermore, given that $CO_2$ is a known green house gas, reducing the $CO_2$ content in the atmospheric emissions of EPTs 100 and 200 may yield additional savings in the form of carbon credits, generate public support, and provide valuable public relations opportunities.

Any additional heating that may be required in EPT 200 may be achieved by additional burning, plasma generators, cavitation pumps, microwaves, ultrasonic waves, nuclear reactors, and various other heating technologies. Some waste materials and emissions of byproducts 136 may not be suitable for electrical power production or liquid fuel creation. These materials may be collected and sold as stock material, or may be disposed in a proper manner. If the concentration of these constituents in by-product 136 exceed regulated amounts, these constituents may be sequestered and/or disposed in a proper fashion.

Figure 4:
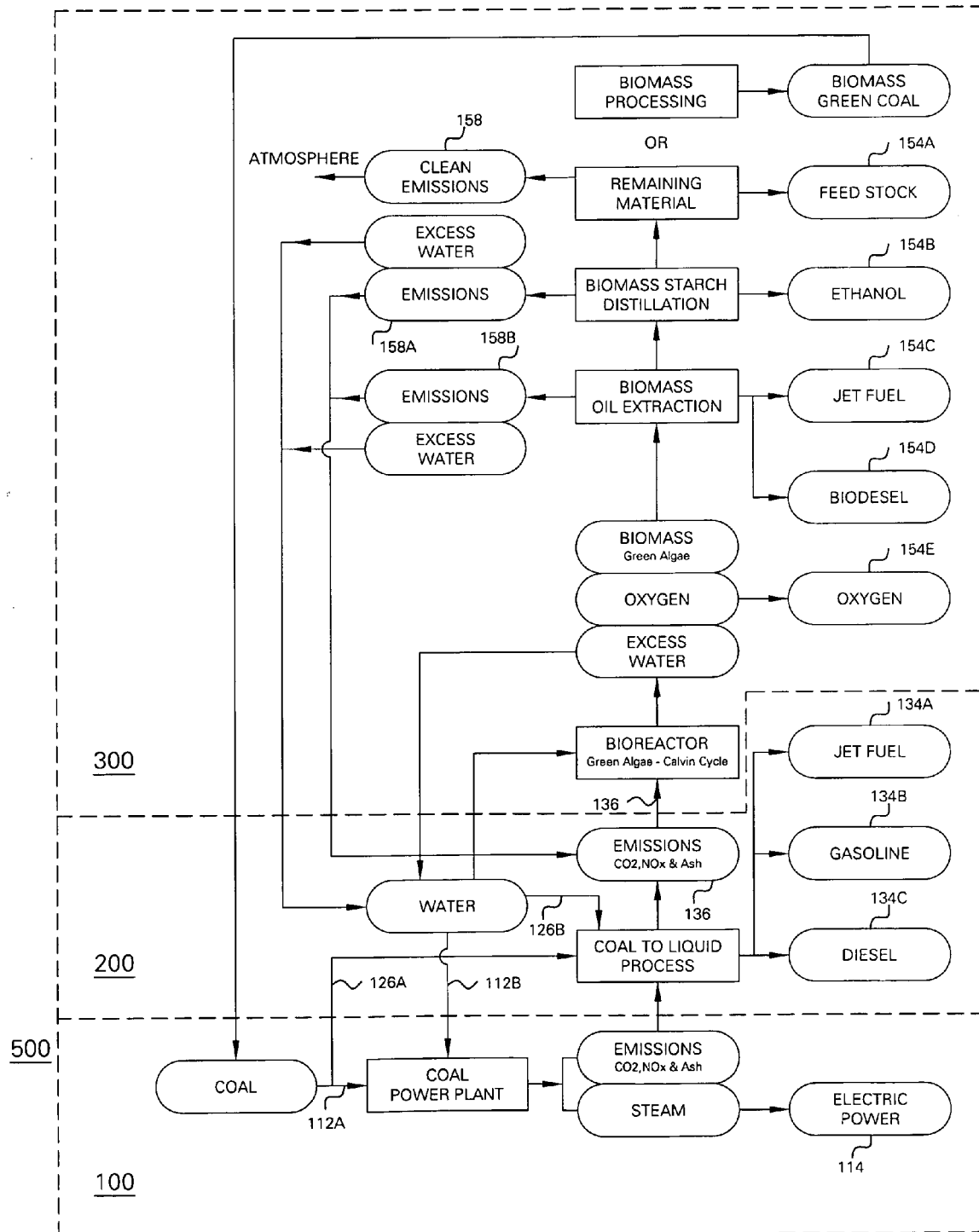
FIG. 4 is a schematic illustration that shows another exemplary EPT that can be used as one of the integrated technologies of FIG. 1 integrated with the EPTs of FIG. 3.

FIG. 4 illustrates a schematic of EPT 300 that may be integrated with coal power plant (EPT 100) and CTL facility (EPT 200) in area 500. EPT 300 may include a biotechnology based energy generation facility. EPT 300 may include any type of energy generation facility that grows and uses plant matter for the creation of different types of energy. Although EPT 300 may include a facility that converts any type of plant matter into energy, in the description that follows EPT 300 will be described as a micro-algae (green algae) based bioreactor. Micro-algae are microscopic single celled plants that grow in an aqueous environment. Like traditional agricultural crops, micro-algae need sunlight, water, and $CO_2$ to grow. However, in general, the productivity of micro-algae per area may significantly higher (such as, for example, 10 to 100 times higher) than traditional agricultural crops, and lower quality water may be used to grow the micro-algae.

Micro-algae may remove $CO_2$ (and $NO_x$) from flue gases through a process commonly known as carbon fixation. In the example shown, byproducts (or emissions) from EPT 100 are fed to EPT 200 and the byproducts from EPT 200 are then fed to EPT 300. In the present disclosure, all or a portion of the byproducts from one or both of EPT 100 and 200 can be fed directly or indirectly to EPT 300. The $CO_2$ and $NO_x$ present in the byproducts may stimulate the growth of the algae. In the embodiment shown in FIG. 4, the $CO_2$ (and $NO_x$) in byproducts 116 and 136 may be converted into organic compounds in a series of biochemical reactions (Calvin cycle and the Krebs cycle) that stimulate the growth of the micro-algae. Since energy production from micro-algae is well known in the art, only those details of the process helpful in describing the disclosed environmentally friendly methods of energy production are described herein.

EPT 300 may include an algae farm that grows micro-algae and uses the biomass created by the micro-algae to produce energy and other products. The micro-algae of EPT 300 may be grown in area 500. In some cases, land surrounding coal power plants and CTL facilities may be infertile land not suitable for traditional food cultivation. However, many micro-algae species may be engineered to thrive in the ecosystem and water of area 500. Utilization of land that does not support traditional faming for micro-algae cultivation may enable energy production using EPT 300, with minimal impact to the food market. The gaseous components of byproducts 136 from EPT 200 may be delivered to EPT 300 and bubbled through bioreactors that grow micro-algae. The micro-algae may consume the $CO_2$ and $NO_x$ in byproducts 136 and release oxygen 154E and water.

The released water may be directed back into the water source of area 500, or may be recycled and used in the bioreactor facility. The oxygen 154E produced may be released into the atmosphere, bottled, or directed to another EPT as input. For instance, the oxygen 154E may be directed to the furnace of a coal power plant to aid in the combustion of coal. The oxygen may also be directed into the gasification or liquefaction process of a CTL facility to aid in the chemical reactions occurring therein. It is also contemplated that the released oxygen may be traded for carbon credits.

The micro-algae may be harvested to produce biomass. This biomass may then be processed to extract oil. Any known process may be used to extract oil from the biomass. In some embodiments, the species of micro-algae grown in EPT 300 may be selected or engineered to increase the oil content of the micro-algae. Since numerous species of micro-algae have oil content higher than 50% of their mass, the micro-algae of EPT 300 may be tailored to produce a significant amount of oil. The oil extracted from the biomass may be processed and refined into various types of fuel, such as jet fuel 154C and bio-diesel 154D. Any emissions that may be produced in the extraction process may be recirculated back into the bioreactor. In some embodiments, water content in these emissions and/or the harvested biomass may be separated. This separated water may be directed to the water source in area 500, or may be used in the power generation facility.

After oil extraction, the remaining biomass may be used to create ethanol 154B. Any process known in the art may be used to create ethanol 154B from the residual biomass. In an exemplary technique, the biomass may be mixed with water to create a mash that may be treated with various enzymes to convert the biomass into simple sugars. The mash may then be treated with yeast that may convert the sugars into ethanol 154B and carbon dioxide 158A. The emitted carbon dioxide 158A may be directed back into the bioreactor. Any excess water produced in this process may be separated and directed back to the water source of area 500, or used in the power generation facility. The ethanol 154B may be further distilled to produce fuels and products such as beverages. The solid byproducts remaining after ethanol extraction may be dried and turned into pellets for feedstock 154A. Any byproducts 158 that are not consumed in EPT 300 or applied to other EPTs 100 or 200 may be released into the atmosphere.

In general, the relative amounts of oil 154C, 154D, 154E, ethanol 154B, and feedstock 154A produced by EPT 300 may be modified as desired. In some embodiments, to increase the nutritional value or energy content of feedstock 154A, the step of ethanol extraction may be eliminated and the biomass residue after oil extraction may be dried into feedstock 154A pellets. In yet other embodiments, the step of oil extraction may also be eliminated and the biomass harvested from the bioreactor may be dried and formed into feedstock 154A. In some embodiments, in place of feedstock 154A, the biomass harvested from the bioreactor may be transformed into a solid fuel, such as green coal. This green coal may be sold as fuel or may be used as fuel in EPT 100 and/or EPT 200.

In general, the size of EPT 300, and the amount of micro-algae farmed in area 500, may depend upon the amount of $CO_2$, $NO_x$, and/or $SO_x$ that may need to be removed from the byproducts, the land available for micro-algae cultivation, and the economics of the application. In some embodiments, EPT 300 may only be large enough to reduce one of the $CO_2$, $NO_x$, or $SO_x$ in byproducts 158 to below an acceptable limit, such as a governmentally regulated limit, or a limit imposed by public opinion. In other embodiments, the size of EPT 300 may be large enough to substantially reduce the amount of all of $CO_2$, $NO_x$, and $SO_x$ released into the atmosphere by EPTs 100, 200 and 300. In all embodiments, the total amount of some or all of $CO_2$, $NO_x$, and $SO_x$ released into the atmosphere by integrated EPTs 100, 200 and 300 is preferably lower than the amount that would be released by EPTs 100, 200 and 300 operating independently. The EPTs 100, 200, and 300 are preferably integrated in a manner that reduces the emissions of the integrated systems well below governmental and/or industry standards, while still providing energy output at commercially competitive pricing.

Although, in some cases, there may be significant benefits if EPTs 100, 200, and 300 are co-located in area 500, this is not a requirement. In some embodiments, conditions associated with the power plant may necessitate EPTs 100, 200, and 300 to be located at different locations. In these cases, integration between EPTs 100, 200, and 300 may still be achieved by transporting (such as, by a pipeline or in containers) the byproducts of one EPT to another EPT.

By integration of power production facilities, gasification/liquefaction fuel production facilities, and biomass emission control, it may be possible to utilize the existing power generation infrastructure to increase fuel supply while reducing harmful emissions. It is believed that biotechnology based energy generation technologies, which are at a relatively immature stage, will continue to be improved, increasing the efficiency and cost effectiveness of combining these technologies. In addition, other electrical power generation systems, such as a nuclear power plant instead of a coal power plant, can be used according to the methods and systems of the present disclosure. A portion of the heat and/or pressure generated in a nuclear system, for example, can be applied as energy input to EPT 200. The generation of noxious gases is thereby lessened, thereby achieving a greater elimination of $CO_2$ waste gases by a given-sized EPT 300. By integrating existing and future biotechnologies with relatively mature EPTs such as coal power plants, nuclear power plants, and CTL facilities, the efficiency and cost effectiveness of biotechnologies may be improved. As biotechnologies for biomass production and pollution control grows, a self sufficient and integrated energy production system which substantially, or even completely, eliminates harmful emissions and produces sufficient green coal to feed the original coal based power plant may be realized.

Figure 5:
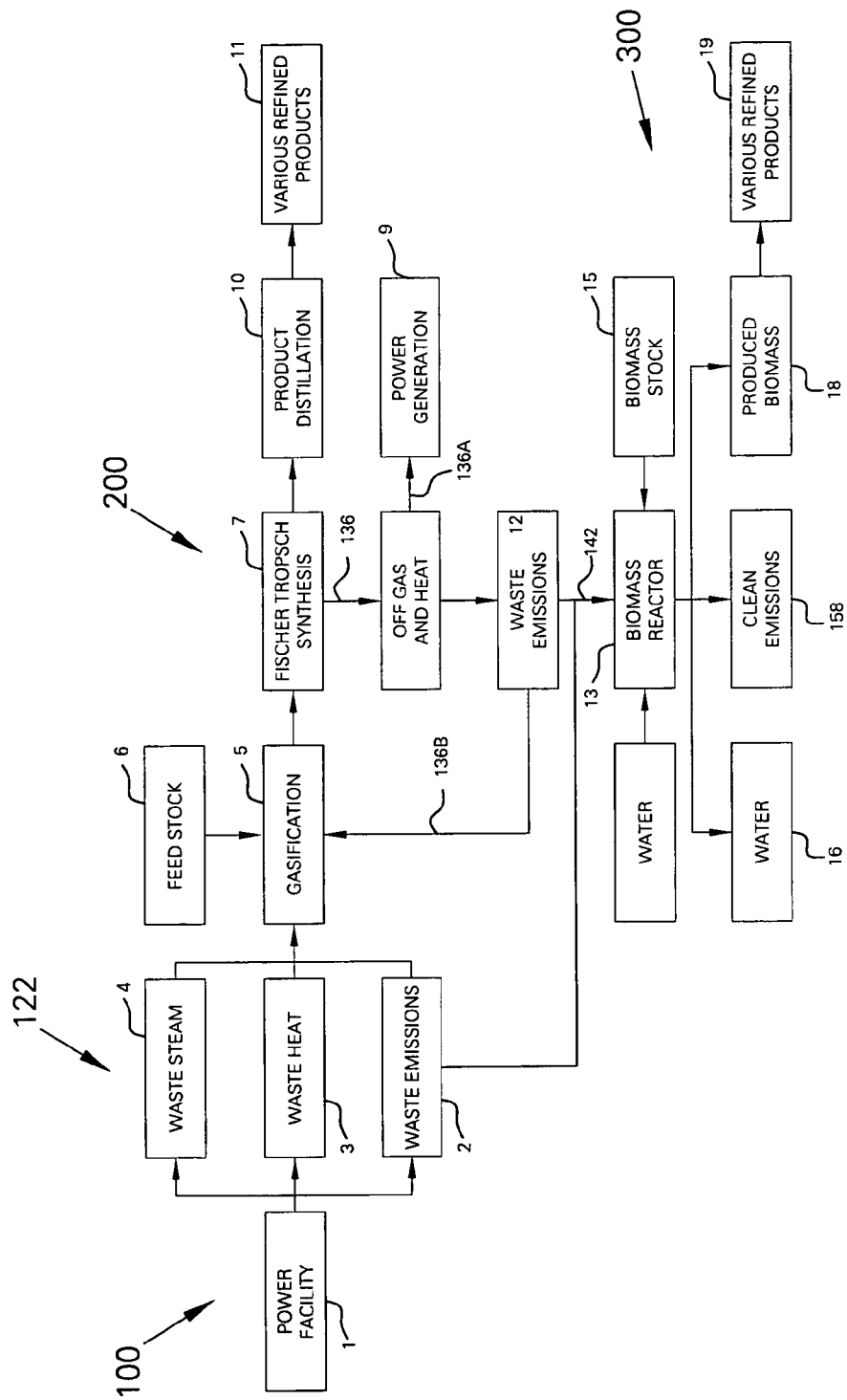
FIG. 5 is a schematic illustration that shows a power generation facility integrated with a coal to liquid (CTL) facility and a biotechnology based energy production facility.

The following paragraphs, and FIGS. 5-17, illustrate some embodiments of the integrated methods of energy production discussed in previous paragraphs. For the sake of brevity, only those aspects of the embodiments which are different from previously described embodiments will be discussed. FIG. 5 is an illustration of another embodiment of an environmentally friendly method of energy production achieved by integrating EPT 100 with a CTL facility (EPT 200) and a biotechnology based energy production plant (EPT 300). EPT 100 may be any power generation facility that may have at least one of the following: waste heat 3, steam 4, or emissions 2, which may be delivered to a downstream EPT. In this embodiment, all or a portion of one or more of the heat 3, steam 4 or emissions 2 from EPT 100 is applied to the gasification system 5. Additional input may be delivered to the system 5 as feedstock from another process 6. The feedstock may also include carbonaceous material, hydrogen or any other stock material that may be needed for process.

The waste products and feed stock delivered to EPT 200 may be heated and pressurized to cause gasification of the stock material to their elemental components (including CO and $H_2$). These elemental components may then be processed and formulated through various Fischer-Tropsch (FT) processes in chambers 7 and 10 into the desired hydrocarbons and chemical products 11. A part 136A of the resulting byproducts 136 may be recovered for additional power generation in generator 9 and a part 136B may be fed back into the gasification process 5. Generator 9 may include any known power generation equipment that generates power from combustible gases and heat. For instance, generator 9 may include, for example, combustion engines and turbine engines. Excess waste materials and gases that are not used for hydrocarbon production or gasification may be separated (byproducts 142) and stored or directed into EPT 300.

EPT 300 may include a bioreactor 13. The bioreactor 13 may be any type of reactor designed for the growth of a specific biological entity, such as micro-algae. In addition to byproducts 142, stock material in the form of biomass stock 15 (e.g. seed or culture) may also be directed into bioreactor 13. As shown, in this embodiment, emissions from both the power facility 1 and the gasification system 5 are applied to the bioreactor 13. Light and nutrients may be also be supplied to the bioreactor 13, along with the biomass stock, to facilitate biomass growth. The biomass in bioreactor 13 may consume the emissions and the nutrients through photosynthesis to grow and create additional biomass 18. This biomass 18 may then be harvested and stored as a food (or feed stock material) or used for additional processing to create a variety of products 19. Some of the resulting byproducts, such as, for example, clean emissions (like oxygen) and water 16, may be environmentally safe and may therefore be released into the environment. Byproducts not disposed into the atmosphere may be captured and handled in accordance with proper disposal methods.

Figure 6:
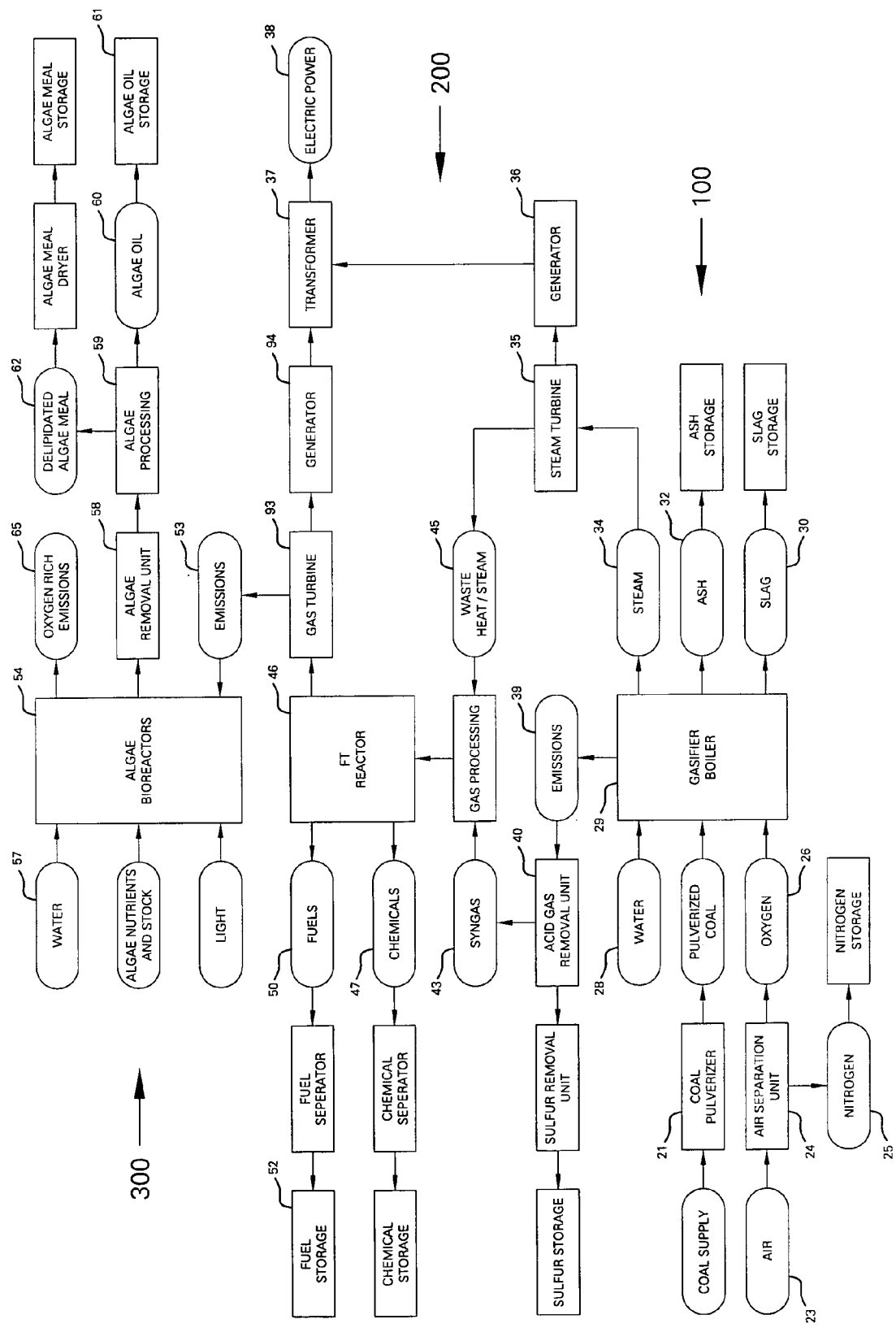
FIG. 6 is a schematic illustration that shows a pulverized coal burning power generation plant integrated with a coal to liquid (CTL) facility and a biotechnology based energy production facility.

FIG. 6 illustrates another embodiment of the disclosed environmentally friendly methods of energy production. In the embodiment of FIG. 6, coal may be transported to a pulverizer 21 through conventional means and prepared for use in a combined cycle gasifier and boiler 29 which utilizes clean water 28 and oxygen 26 to burn the pulverized coal. The oxygen may be provided from atmospheric air 23 and separated by an air separation unit 24 which may isolate nitrogen 25 and oxygen 26. The separation of nitrogen may reduce the amount of $NO_x$ emissions formed as a result of burning the coal.

The combustion of coal can be described as: $C_xH_y + O_2 \rightarrow CO_x + H_2O + Heat$. The presence of sulfur (S) and nitrogen (N) in the coal may yield $SO_x$ and $NO_x$ in the emissions. Other impurities and heavy metals may result in the formation of various types of slag 30 and ash 32 during burning. This slag 30 and ash 32 may settle at the bottom of the gasifier and may be isolated and stored. Pipes in the gasifier may contain water which may get heated and form steam 34. This steam may be used to spin the blades of a steam turbine 35. The turbine 35 may be connected to a generator 36 which may generate electrical power. The electrical power produced may then be carried to a transformer 37 which may step up and supply the power to electric grid 38. Electrical power produced by this process may also be used for sub processes and units that require electrical power for function or monitoring.

The remaining emissions 39 from the gasifier boiler may contain carbon oxides ($CO_x$) sulfur oxides ($SO_x$) nitrogen oxides ($NO_x$) water ($H_2O$ in the form of steam) along with small amounts mercury (Hg) and trace amount of other impurities from the coal. These compounds and elements are typically under high heat and pressure. They may pass through a typical acidic gas removal unit 40 to separate $SO_x$ from the emissions. The emissions may then be processed to separate and store sulfur. After the sulfur has been removed, the remaining syngas 43 may be directed to the FT reactor 46 to be processed into various chemicals and hydrocarbons. If additional heat or steam is desired, the waste heat and steam 45 from the steam turbine 35 may be used. Extraction and transportation of waste heat and steam from steam turbine 35 to the FT reactor 46 may be achieved by known methods of piping or other means.

The FT reactor 46 of EPT 200 may contain various catalysts to convert the syngas into the various desired products. Heavy chemicals 47 may be separated and stored. Once stored it may be sold as a stock material or disposed. The lighter formations and hydrocarbons may be processed into various grades of fuel 50. These fuels may be separated and transferred to storage tanks 52. These storage facilities may be located near the processing facility or may be transferred by pipeline to a main fuel distribution location. Some of the resulting gases from FT reactor 46 may be directed to one or more gas turbines 93 to allow for the expansion of these hot high pressure gases. These turbines 93 may spin a generator 94 to produce additional electrical power that may also be stepped up by transformer 37 and supplied to the power grid 38. Emissions 53 from turbine 93 may then be directed to a bioreactor 54 growing micro-algae or other suitable organisms.

The emissions 53 that may be too hot for use in bioreactor 54 may be run through pipes to warm the facilities of bioreactor 54 and maintain temperature conditions suitable for growth of the micro-algae. Emissions 53 cooled to the proper temperature may be bubbled through bioreactor 54. The stock algae and algae nutrients not found in the emissions 53 may be fed into bioreactor 54 along with clean or waste water 57. During the day, sunlight may be provided so as to allow for photosynthesis with the algae. At night, or during times of low sunlight, power from the generator 36 of EPT 100 may be used to light the bioreactor 54.

Once the water reaches a certain consistency due to the growth of algae, the water may be flowed through a removal unit to filter out the algae biomass 58 for storage or additional processing 59. This algae may be sold as feedstock, or may be delipidated 62 to separate algae oil from the resulting algae meal 62. The algae meal may be dried with waste heat from various processes 63 and stored and sold as a separate product 64. The algae oil 60 may be stored in a storage device 61 to be sold or processed into various types of biofuels. When algae grows, it may produce oxygen. This oxygen may be combined with any unused emissions 65 to ensure compliance with regulations. The resulting oxygen rich emission may also be fed back to air separation unit 24 or gasifier boiler 29.

Figure 7:
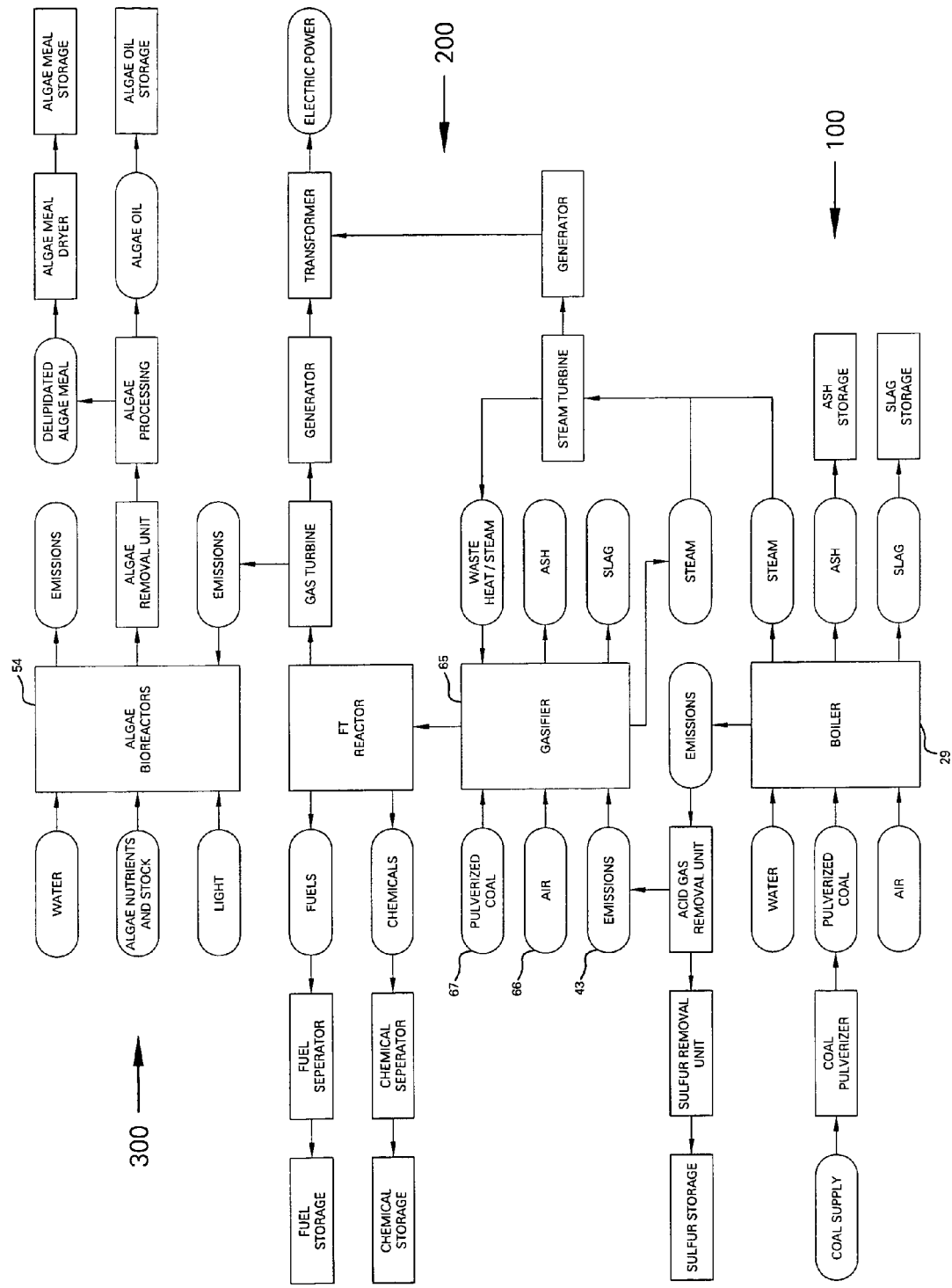
FIG. 7 is a schematic illustration that shows another embodiment of a coal power generation facility integrated with a coal to liquid (CTL) facility and a biotechnology based energy production facility.

FIG. 7 illustrates another embodiment of the disclosed environmentally friendly methods of energy production. The process of the embodiment of FIG. 7 is similar to that in the embodiment of FIG. 6, except that EPT 100 of FIG. 6 represents a typical existing coal power plant which may not have integrated air separation units, and use traditional boilers for combustion. This system may require additional heat to be supplied to the gasifier unit 65 for full gasification of the supplied coal 67. Emissions 43 and air 66 or oxygen from an air separation unit may be directed into gasifier 65 along with pulverized coal 67. This coal 67 may be combusted in gasifier 65. The source of the coal for the gasifier 65 and the boiler 29 may be the same. EPT 200 of FIG. 7 may produce larger amounts of emissions from the gasifier 65 as compared to the system of FIG. 6. In some embodiments, multiple bioreactors 54 may be used to handle such larger volumes of emissions.

Figure 8:
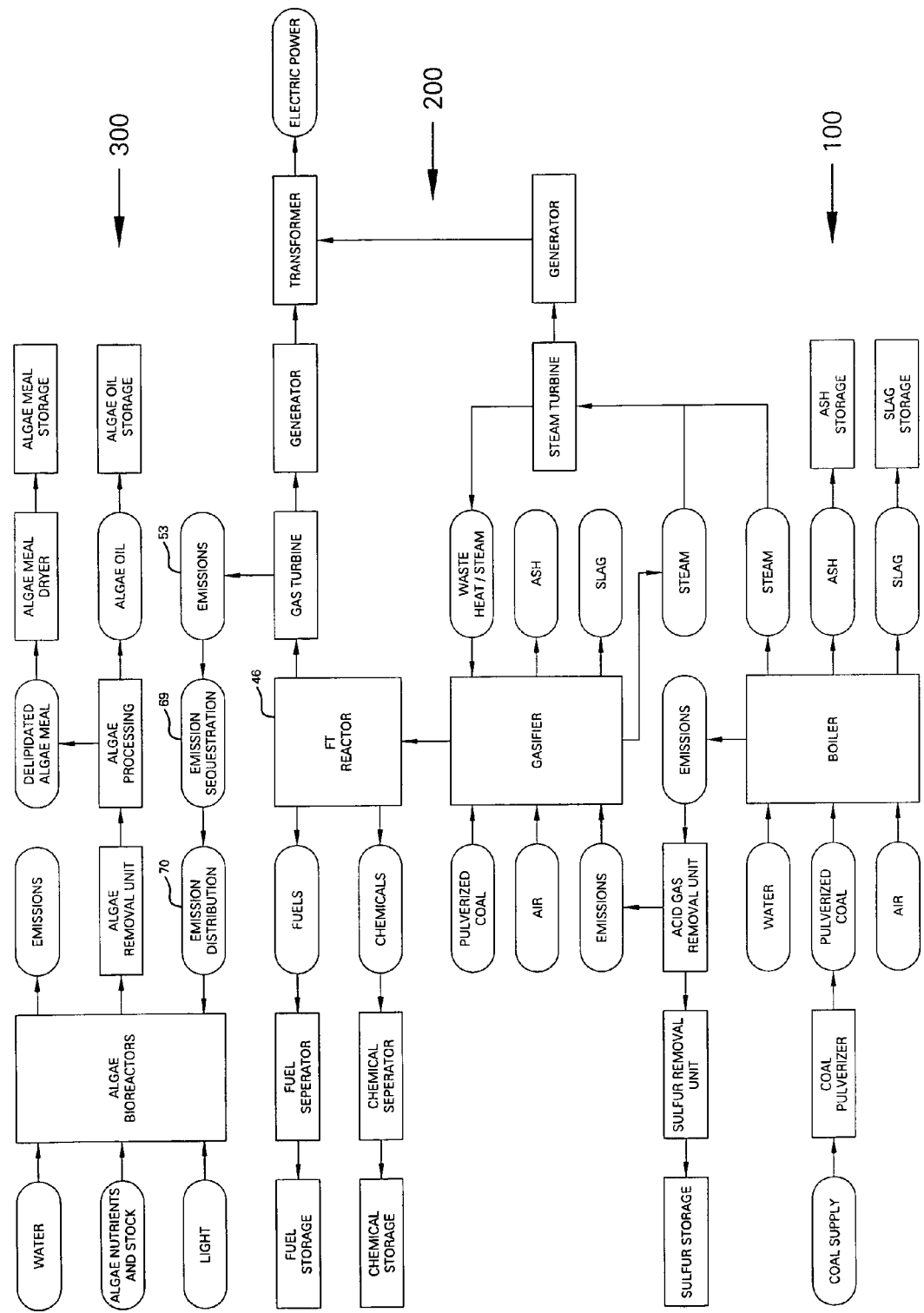
FIG. 8 is a schematic illustration that shows an embodiment of three integrated energy production technologies where some of the byproducts are sequestered.

FIG. 8 illustrates another embodiment of the disclosed environmentally friendly methods of energy production. The embodiment of FIG. 8 is similar to the embodiment of FIG. 7, but emissions 53 from the FT reactor 46 of EPT 200 may be temporally sequestered in tanks 69 for distribution. By making use of temporary sequestration, it may be possible to divert the emissions 70 for a variety of uses. Some portions of the emissions may be transferred to oil fields for crude oil recovery, while other portions may be directed as input to biomass production facilities (EPT 300).

Figure 9:
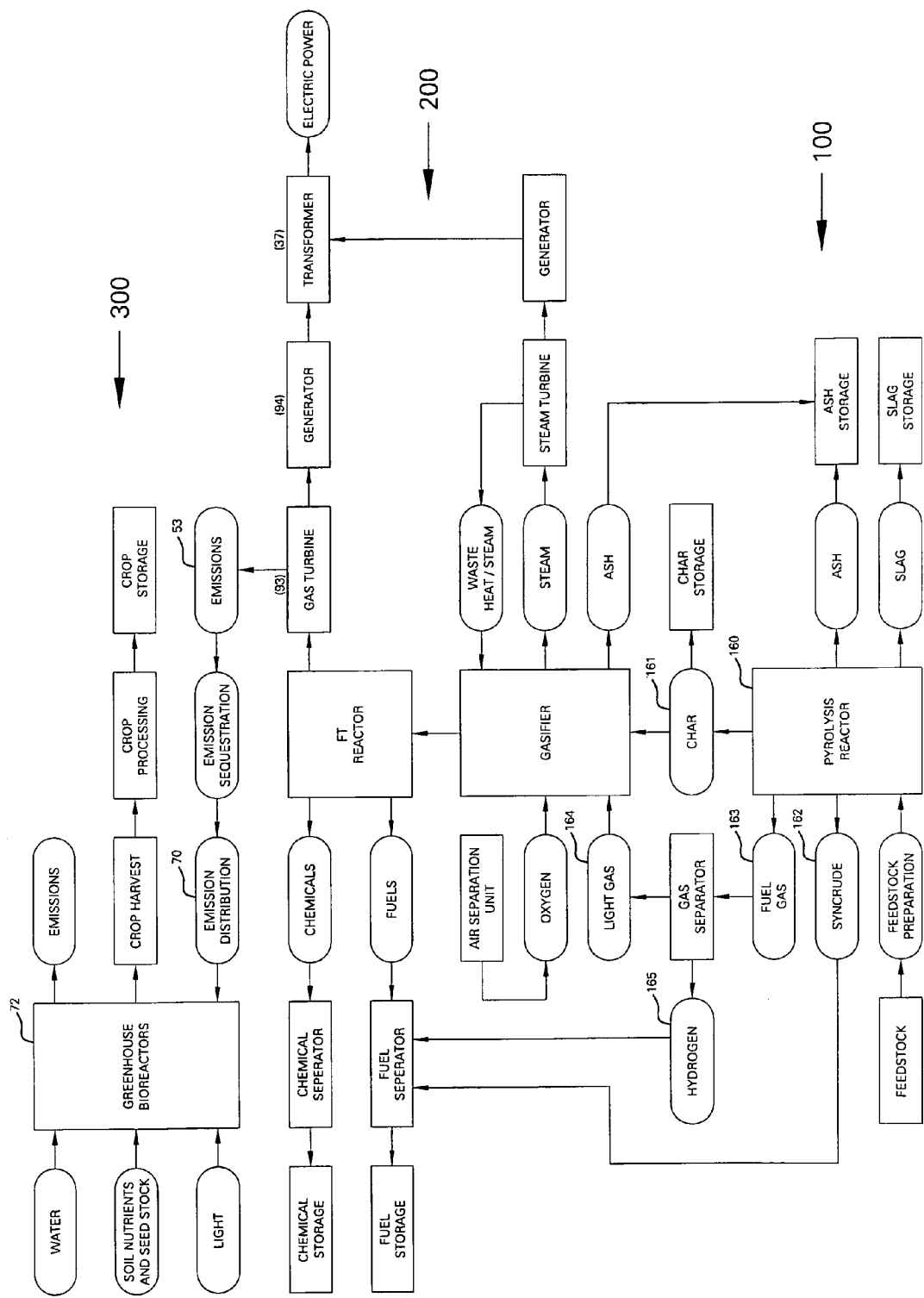
FIG. 9 is a schematic illustration that shows a pyrolysis reactor facility integrated with a coal to liquid (CTL) facility and a seed crop based biomass generation facility.

FIG. 9 illustrates another embodiment of the disclosed environmentally friendly methods of energy production. The embodiment of FIG. 9 is similar to the embodiment of FIG. 8, except that in the embodiment of FIG. 9, a pyrolysis reactor 160 is used for the low temperature carbonization of carbonaceous feedstock. When carbonaceous feedstock is subjected to temperatures near or above 500° C., chemical decomposition may occur in the material, resulting in fuel gas 163 and syncrude liquid 162, and leaving high carbon content char. This process is commonly known as pyrolysis. The fuel gas may be separated into hydrogen 165 for fuel processing and light gas 164 for gasification. The char 161 may be used as a carbon feedstock for a gasifier, or separated and stored for other uses such as the creation of terra preta, which is a nutrient rich soil that may be used in the biomass facility in EPT 300. FIG. 9 also deviates from FIG. 8 in that the emissions 53 from EPT 200 are directed to a biomass facility (EPT 300) that uses seed crop instead of algae. With the use of emission distribution 70, the emission gases may be distributed between multiple greenhouse facilities 72 that grow seed crops. In these greenhouse facilities 72, seed crops may be grown using traditional methods of agriculture. Since CO2 is beneficial for the growth of plants, directing emission gasses from an upstream EPT to these greenhouses may enhance growth of the seed crops while reducing the CO2 emitted into the atmosphere.

Figure 10:
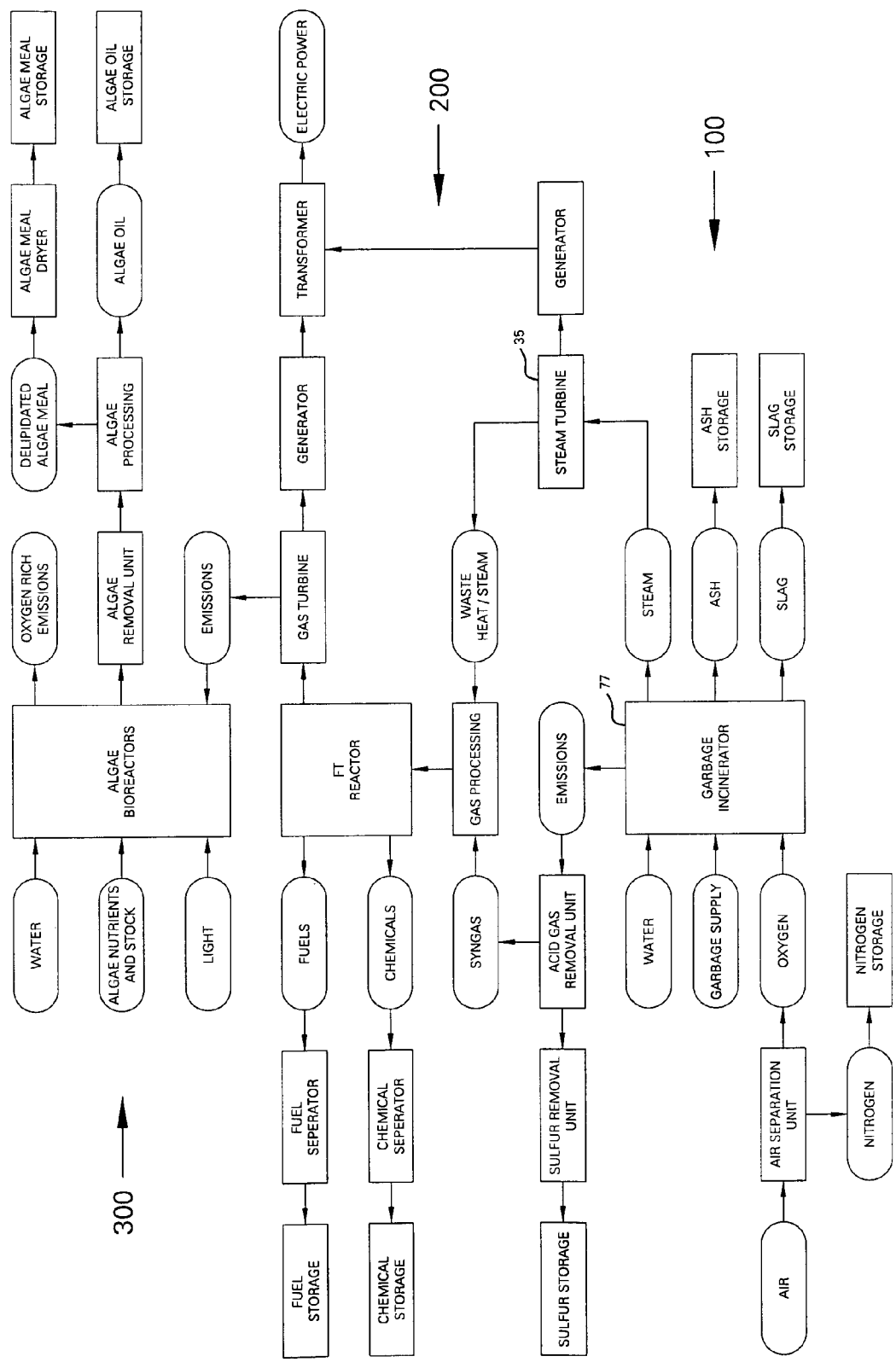
FIG. 10 is a schematic illustration that shows a garbage incinerator based power generation facility integrated with a coal to liquid (CTL) facility and a biotechnology based energy production facility.

FIG. 10 illustrates another embodiment of the disclosed environmentally friendly methods of energy production. The embodiment of FIG. 10 is similar to the embodiment of FIG. 9 except that, in the embodiment of FIG. 10, a garbage or waste incinerator 77 is used to boil the water in EPT 100. In this embodiment, the heat of combustion of waste products in the incinerator 77 may create the steam that drives turbine 35 of EPT 100. When waste buried in landfills biodegrades, methane (another green house gas) may be created and discharged into the atmosphere. This waste may be used as a combustion source in an EPT. By using waste products for combustion, it may be possible to reduce, and even eliminate, the methane gas released into the atmosphere. Additionally, energy (electric power or fuel) may be produced by burning waste in an EPT. The $CO_2$ produced by the combustion process may be eliminated or reduced as described earlier.

Figure 11:
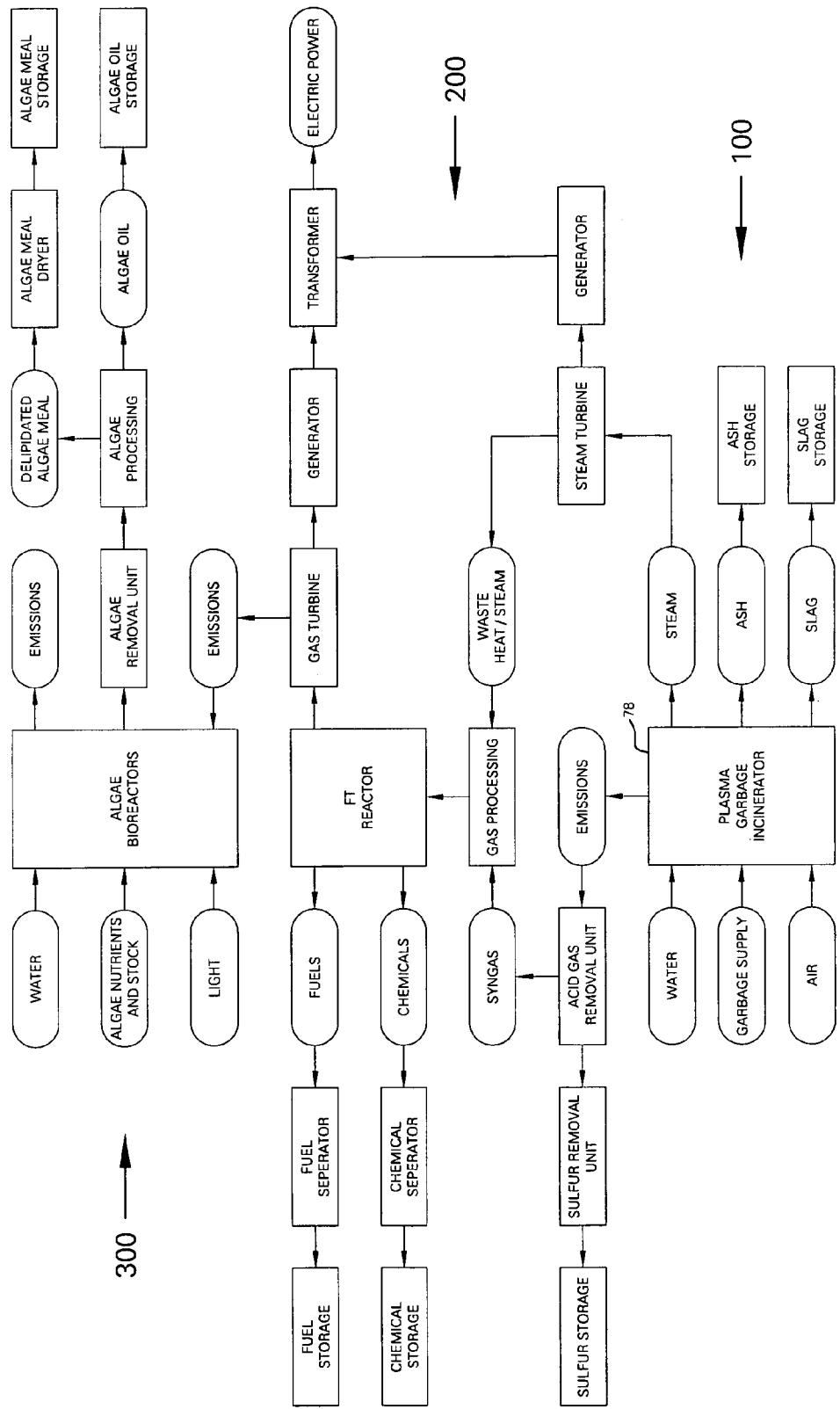
FIG. 11 is a schematic illustration that shows a plasma incinerator based power generation facility integrated with a coal to liquid (CTL) facility and a biotechnology based energy production facility.

FIG. 11 illustrates another embodiment of the disclosed environmentally friendly method of energy production. The embodiment illustrated in FIG. 11 is similar to that illustrated in FIG. 10 except that a plasma incinerator 78 is used to burn the waste products in EPT 100 of FIG. 11. As a plasma incinerator operates at higher temperatures, it may be possible to gasify a wider range of materials that may be present in the waste stream without the need for separation.

Figure 12:
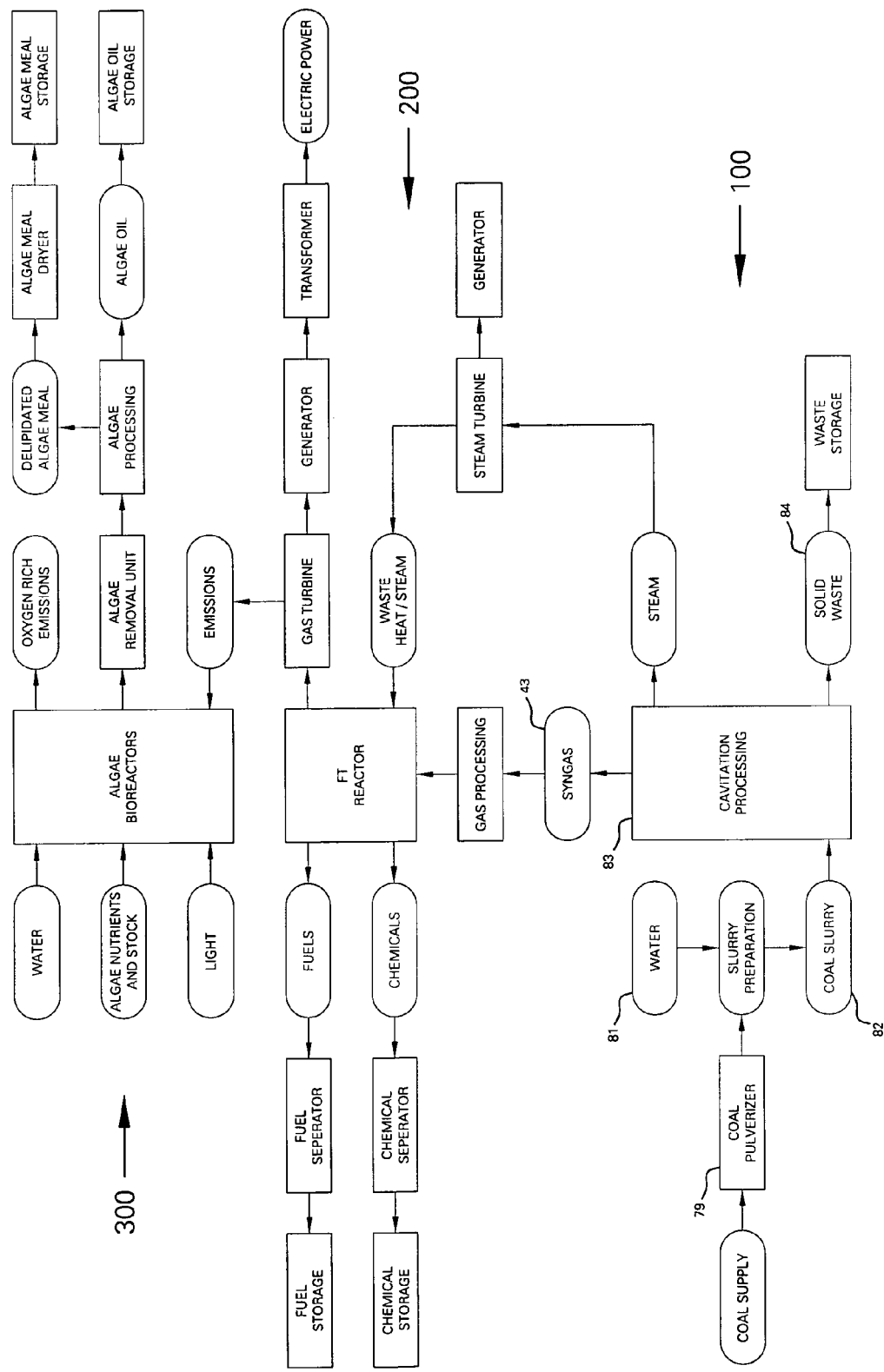
FIG. 12 is a schematic illustration that shows a cavitation processing based energy generation facility integrated with a coal to liquid (CTL) facility and a biotechnology based energy production facility.

FIG. 12 illustrates another embodiment of the disclosed environmentally friendly methods of energy production. In the embodiment of FIG. 12, a cavitation processing unit 83 may be used in EPT 100. The cavitation processing may utilize coal slurry 82 for processing. The coal slurry 82 may be prepared by mixing water 81 or solvent and other liquids with pulverized coal 79. This slurry 82 may be fed into cavitation pumps which use the release of heat from the collapse of small microscopic bubbles to generate heat and pressure. This heat and pressure may result in converting the coal in the slurry into syngas 43. Other constituents of the slurry may be separated as solid waste 84.

Figure 13:
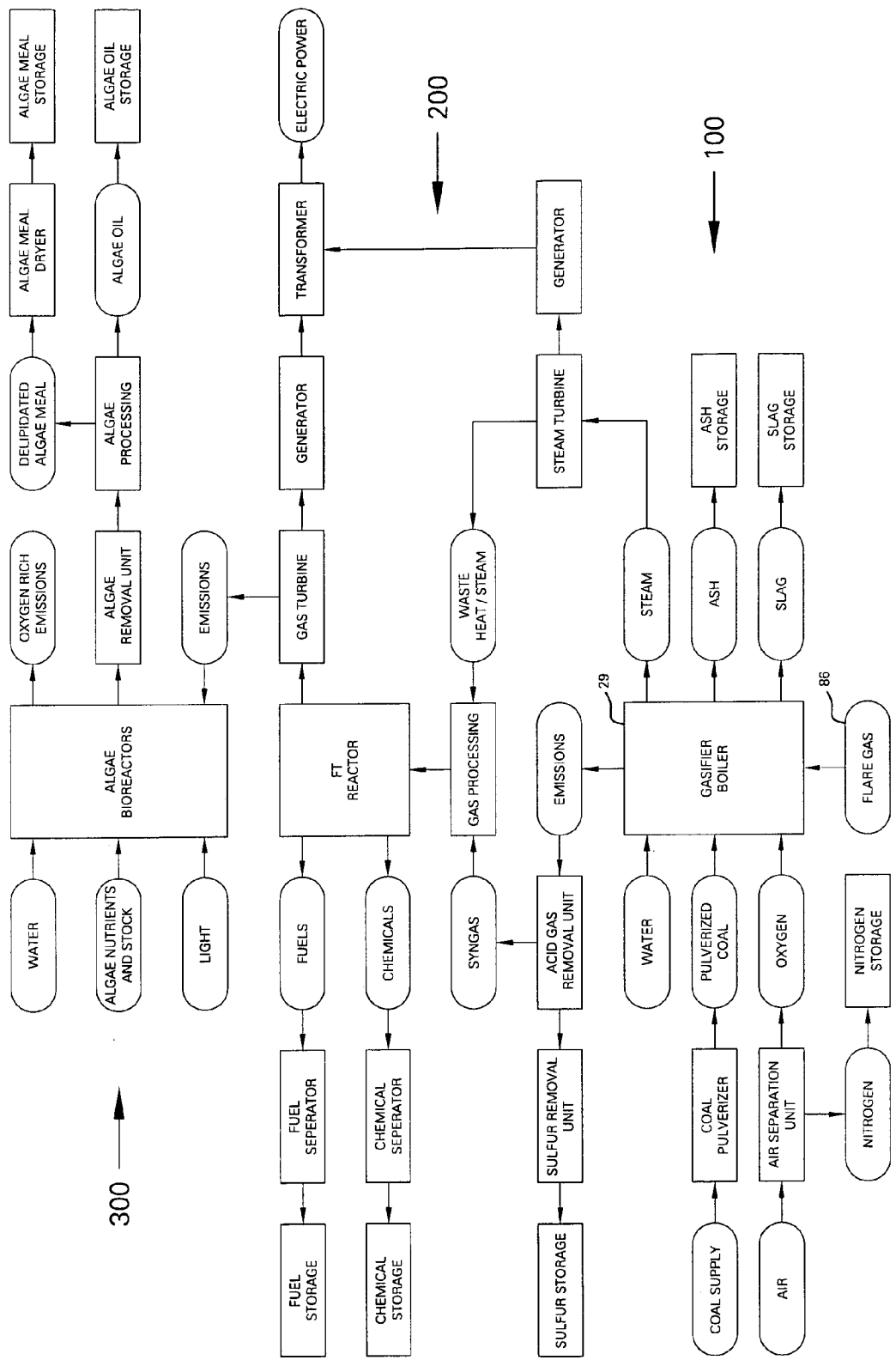
FIG. 13 is a schematic illustration that shows an energy generation facility utilizing flare gas, integrated with a coal to liquid (CTL) facility and a biotechnology based energy production facility.

FIG. 13 illustrates another embodiment of the disclosed environmentally friendly method of energy production. In the embodiment of FIG. 13, flare gas 86 may also be introduced into the gasifier boiler 29 of EPT 100. Flare gas may be any waste gas that is a result of chemical processing. Flare gas may contain methane in addition to various other hydrocarbon constituents. By burning flare gas 86 in the gasification boiler 29, release of GHGs and pollutants into the atmosphere may be further reduced.

Figure 14:
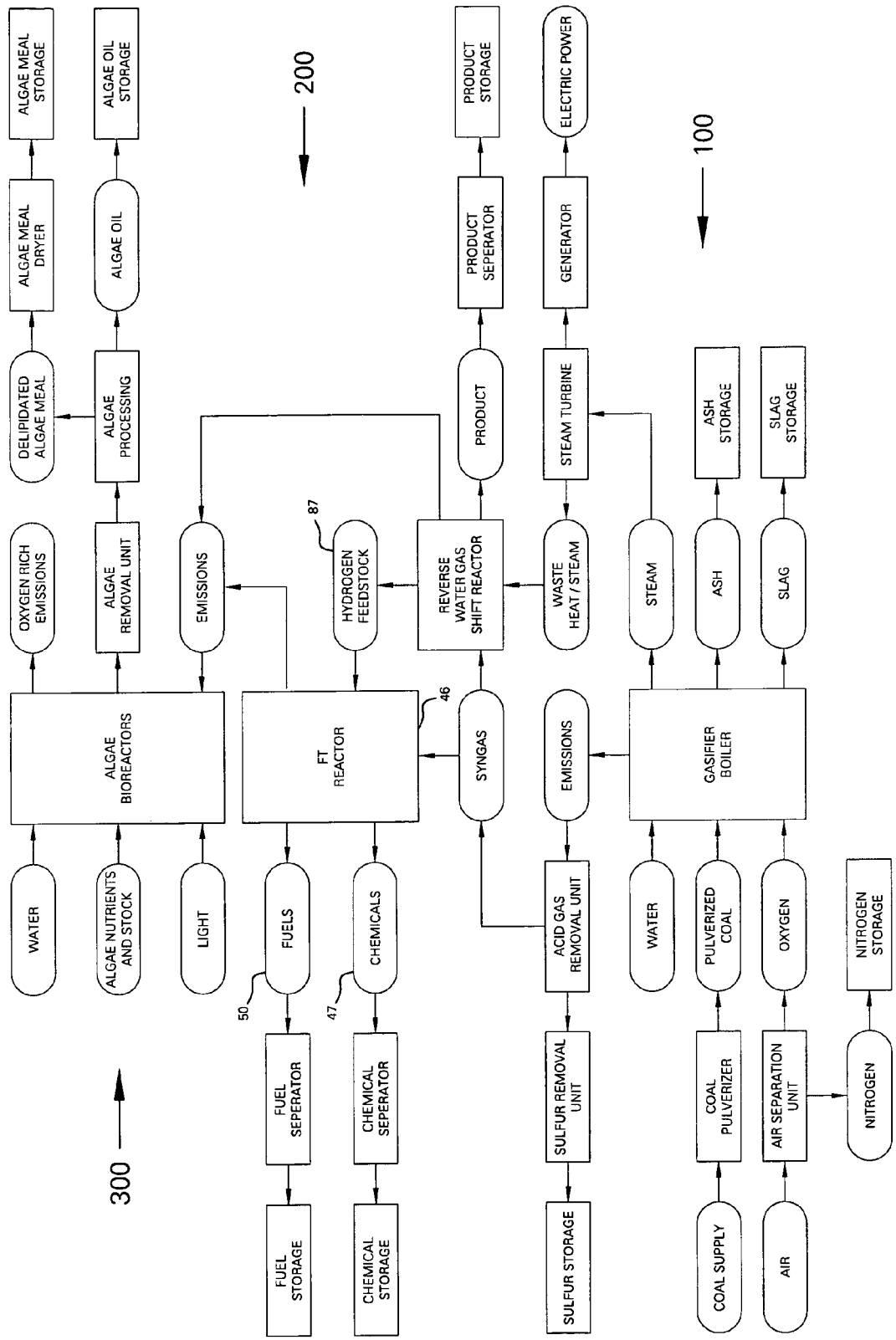
FIG. 14 is a schematic illustration that shows a power generation facility, integrated with a coal to liquid (CTL) facility that uses hydrogen feedstock, and a biotechnology based energy production facility.

FIG. 14 illustrates another embodiment of the disclosed environmentally friendly method of energy production. In the embodiment of FIG. 14, hydrogen feedstock 87 may also be introduced into the FT reactor 46 of EPT 200. This additional hydrogen may create a hydrogen rich environment for hydrocarbon (fuels 50 and chemicals 47) formation. This hydrogen feedstock 87 may be generated and delivered to the FT reactor 46 by methods known in the art. The increased hydrogen in the FT reactor 46 may increase the amount of carbon monoxide formed by the break down of coal, and may also enable the reduction of increased amounts of $CO_2$ (contained in the emissions) into CO. Increased amounts of CO and $H_2$ may increase the amount of syngas formed in the FT reactor 46. The excess hydrogen in the FT reactor 46 may thus increase the production of fuel in EPT 200.

Figure 15:
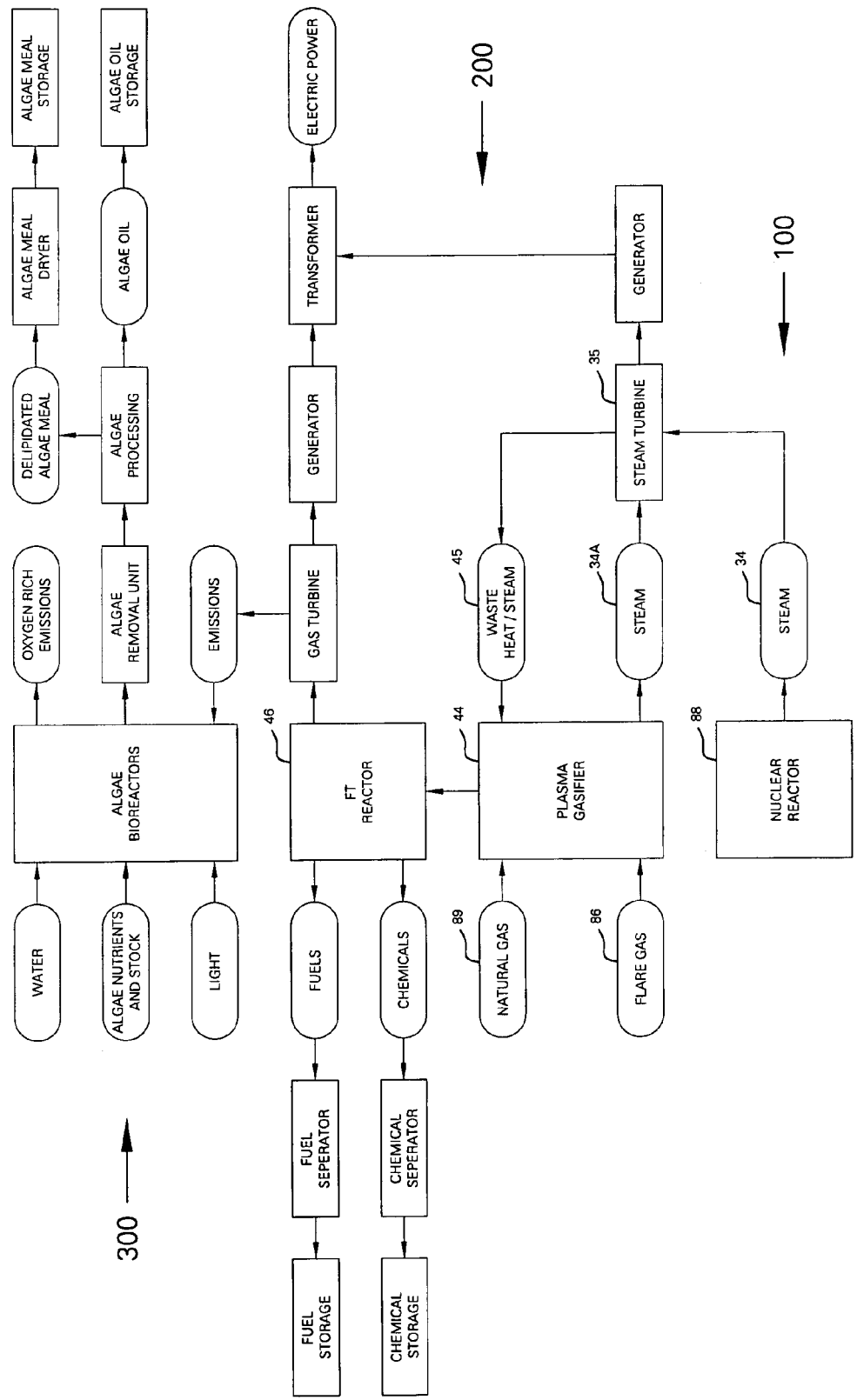
FIG. 15 is a schematic illustration that shows a nuclear power generation facility integrated with a coal to liquid (CTL) facility and a biotechnology based energy production facility.

FIG. 15 illustrates another embodiment of the disclosed environmentally friendly methods of energy production. In the embodiment of FIG. 15, waste steam 34 from a nuclear power plant 88, along with natural gas 89, and flare gas 86 may be directed into a plasma gasifier 44. The natural gas 89 and flare gas 86 may provide the carbon, and the steam 34 from the nuclear reactor power plant may provide the hydrogen, needed for the formation of hydrocarbons. The plasma gasifier 44 may heat the gases and steam to the required temperature and pressure for the FT reactor 46. Water jackets in the plasma gasifier 44 may create additional steam 34A that may supplement the steam 34 from nuclear reactor 88 and used to spin steam turbine 35. The exhaust steam 45 may then be directed into the gasifier 44 as hydrogen feedstock.

Figure 16:
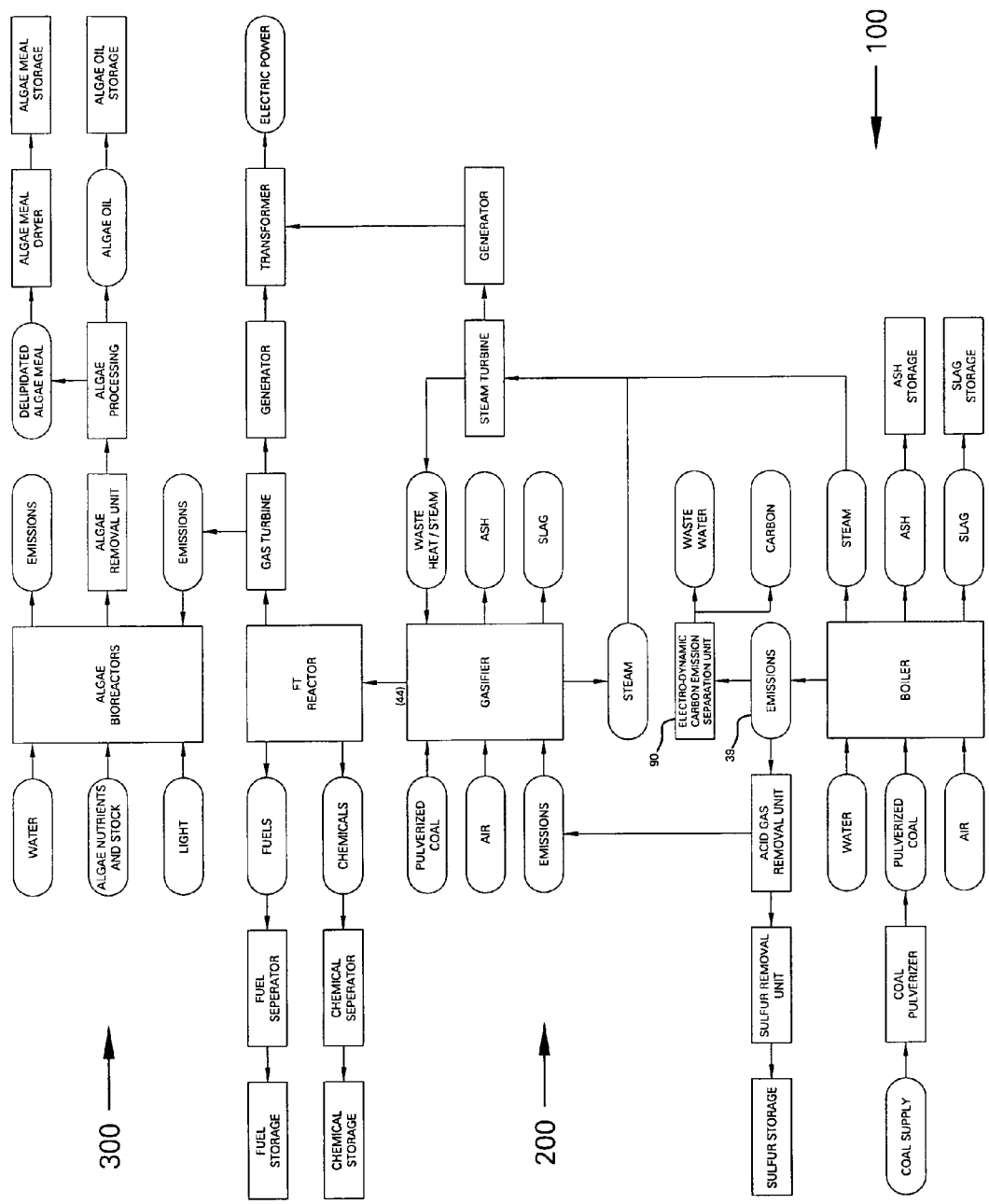
FIG. 16 is a schematic illustration that shows a coal power plant utilizing a carbon emission separation unit integrated with a coal to liquid (CTL) facility and a biotechnology based energy production facility.

FIG. 16 illustrates another embodiment of the disclosed environmentally friendly method of energy production. In the embodiment of FIG. 16, an electro-dynamic carbon emission separation unit 90 may be used to remove carbon and water from the emissions 39 of EPT 100. Removal of the carbon from emissions 39 may reduce the total $CO_2$ exhausted into the atmosphere from the integrated power plant. Exemplary processes that may be used to electrodynamically remove airborne carbon and sulfur dioxides are described in International Patent Publication WO/2005/046877, which is incorporated by reference herein.

Figure 17:
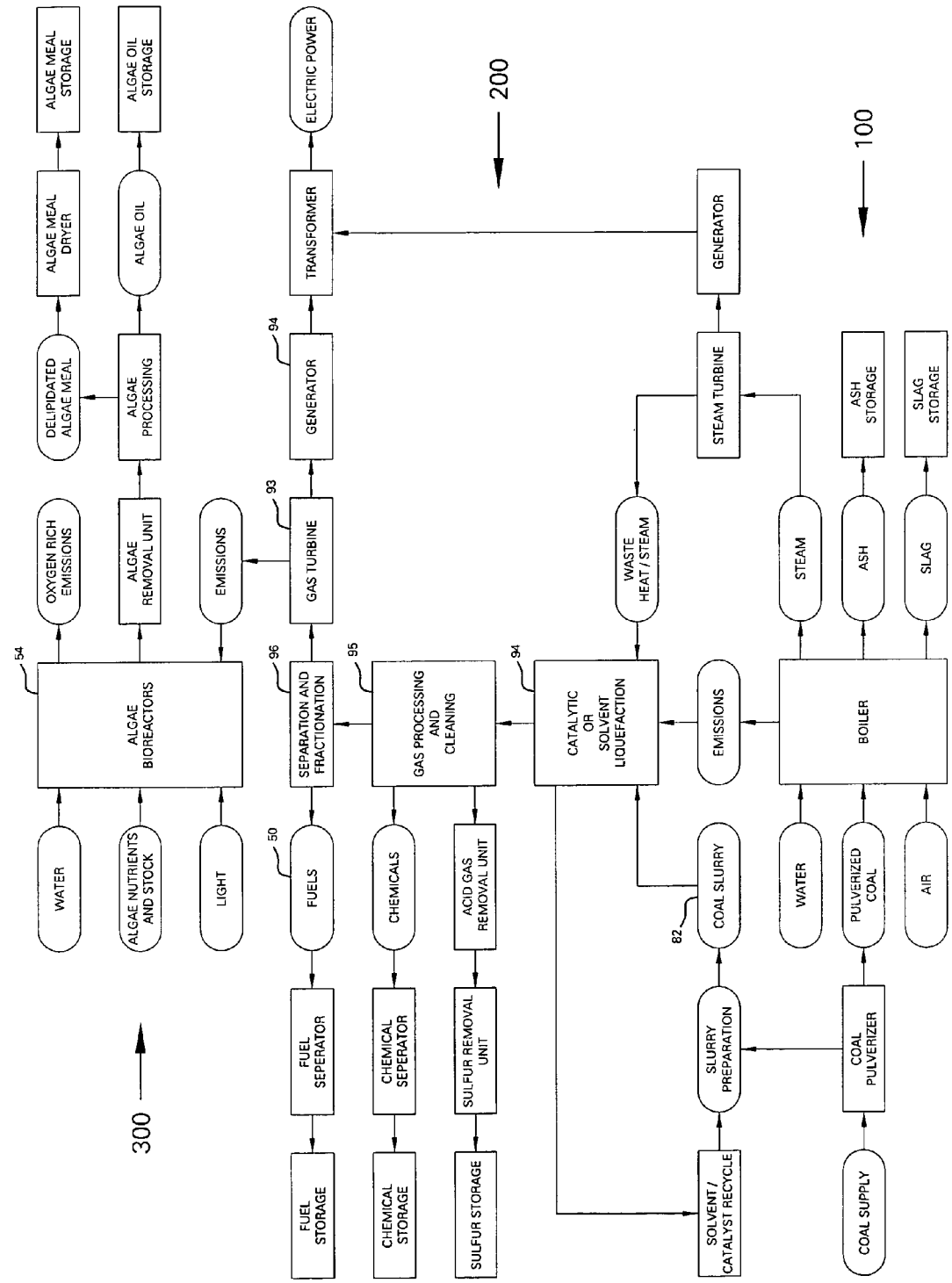
FIG. 17 is a schematic illustration that shows a coal power plant integrated with a carbonaceous liquefaction processing unit and a biotechnology based energy production facility.

FIG. 17 illustrates another embodiment of the disclosed environmentally friendly method of energy production. In the embodiment of FIG. 17, a coal slurry 82 is prepared and directed to a direct catalytic or solvent carbonaceous liquefaction processing unit 94. A solvent or a catalyst may be mixed with the slurry 82 before being directed to the liquefaction processing unit 94. Liquefaction processing unit 94 converts the coal in the slurry 82 to synthetic crude oil ("syncrude"), which may be directed into a liquid processing and cleaning unit 95. After extraction of chemicals and acid from the liquid, the remaining syncrude may be directed into a separation and fractionation unit 96 which may yield various fuel products 50. Some of the waste energy in the emissions from the separation and fractionation unit 96 may be recovered through a gas turbine 93 and a generator 94, before these emissions may be directed into a bioreactor 54.

As is evident from the disclosed embodiments, existing energy production facilities may be integrated together to improve their operational efficiency while decreasing environmentally harmful emissions. These existing energy production facilities are integrated together in a manner such that the strengths of one energy production facility is used to balance the weakness of another energy production facility. By integrating multiple energy production technologies, the total amount of environmentally harmful GHGs released to the atmosphere will be lower than the amount that would be released by operating these energy production technologies independently (that is, in an un-integrated manner).

It will be apparent to those skilled in the art that various modifications and variations can be made to the disclosed environmentally friendly methods of energy production without departing from the scope of the disclosure. Other embodiments will be apparent to those skilled in the art from consideration of the specification. It is intended that the specification and examples be considered as exemplary only, with a true scope being indicated by the following claims and their equivalents.

What is claimed is:

1. A process of energy production, comprising:
   integrating three or more energy production technologies such that a first byproduct of a first energy production technology is applied to a second energy production technology and a second byproduct of the second energy production technology is applied to a third energy production technology, the first energy production technology being a power generation facility, the second energy production technology being a carbonaceous feedstock gasification facility, and the third energy production technology being a bioreactor facility; and
   operating the integrated energy production technologies to produce energy such that at least a portion of the first byproduct is utilized in an operation of the second energy production technology and a portion of the second byproduct is utilized in an operation of the third energy production technology.

2. The process of claim 1, wherein the first byproduct and the second byproduct are selected from a group consisting of steam, heat, and gaseous emissions, the gaseous emissions including one or more of $CO_2$, an oxide of sulfur, and an oxide of nitrogen.

3. The process of claim 2, wherein the first byproduct includes one or more of steam and heat, and the second byproduct comprises gaseous emissions that include one or more of $CO_2$, the oxide of sulfur, and the oxide of nitrogen.

4. The process of claim 3, wherein operating the integrated energy production technologies reduces a cost of implementation of at least one of the three or more energy production technologies as compared to a case where the three or more energy production technologies are operated independently.

5. The process of claim 4, wherein operating the integrated energy production technologies includes reducing a concentration of at least one of the $CO_2$, the oxide of sulfur, or the oxide of nitrogen as compared to the case where the three or more energy production technologies are operated independently.

6. The process of claim 5, wherein at least two of the three or more energy production technologies are located in close proximity to each other to share infrastructure.

7. The process of claim 6, wherein the first energy production technology is selected from a group consisting of a coal power plant and a nuclear power plant.

8. The process of claim 1, wherein utilizing the first byproduct includes using the first byproduct in a chemical reaction to produce a fuel gas in the second energy production technology, and utilizing the second byproduct includes using the second byproduct in a biochemical reaction to grow organic matter.

9. A process for producing energy, comprising:
   integrating a power generation facility, a carbonaceous feedstock gasification facility, and a bioreactor facility to produce electric power, liquid fuel, and biomass; and
   utilizing a byproduct of one or more of the said facilities to assist in the production of one or more of the electric power, the liquid fuel, and the biomass.

10. The process of claim 9, wherein at least one of waste heat, waste steam and gaseous emissions of the power generation facility is used in the carbonaceous feedstock gasification facility to assist in the production of liquid fuel.

11. The process of claim 10, wherein gaseous emissions from the carbonaceous feedstock gasification facility are used to assist in the production of biomass in the bioreactor facility.

12. The process of claim 11, wherein gaseous emissions of the power generation facility and the carbonaceous feedstock gasification facility are used to assist in the production of biomass in the bioreactor facility.

13. The process of claim 9 wherein a portion of the byproduct is sequestered for future use.

14. The process of claim 9, wherein the power generation facility includes one of a coal burning power generation facility, a nuclear power generation facility, a garbage incinerator, a plasma incinerator, a cavitation processing unit, and a pyrolysis reactor.

15. The process of claim 14, wherein the coal burning power generation facility includes a combined cycle gasifier and boiler having an air separation unit.

16. The process of claim 14, wherein the pyrolysis reactor provides char to the carbonaceous feedstock gasification facility, 17. The process of claim 9, wherein at least the power generation facility and the carbonaceous feedstock gasification facility are located in close proximity to each other to reduce operating costs.

18. The process of claim 9, wherein the byproduct includes one or more of steam, heat, $CO_2$, an oxide of sulfur, and an oxide of nitrogen.

19. The process of claim 18, wherein integrating the power generation facility, the carbonaceous feedstock gasification facility, and the bioreactor facility reduces a concentration of at least one of the $CO_2$, the oxide of sulfur, or the oxide of nitrogen as compared to a case where the power generation facility, the carbonaceous feedstock gasification facility, and the bioreactor facility are not integrated.

20. The process of claim 9, wherein the carbonaceous feedstock gasification facility includes a liquefaction processing unit, and a coal slurry is directed to the liquefaction processing unit.

21. The process of claim 20, wherein the liquefaction processing unit converts a portion of the coal slurry to synthetic crude oil.

22. A method of energy production, comprising:
producing a first energy and first byproducts in a first energy production technology, wherein the first energy includes electric power;
utilizing at least a portion of the first byproducts to produce a second energy and second byproducts in a second energy production technology; and
utilizing at least a portion of the third byproducts to produce a third energy and third byproducts in a third energy production technology,
wherein, the first byproducts, the second byproducts, and the third byproducts include at least one of $CO_2$, an oxide of sulfur, and an oxide of nitrogen, and
wherein utilizing the first byproducts and utilizing the second byproducts reduces a concentration of at least one of $CO_2$, the oxide of sulfur, or the oxide of nitrogen released to atmosphere as compared to a case where the first byproducts and second byproducts are not so utilized.

23. The method of claim 22, wherein utilizing the first byproducts and utilizing the second byproducts lowers an operating cost of at least one of the first energy production technology, the second energy production technology, or the third energy production technology.

24. The method of claim 22, wherein the second energy production technology is selected from a group comprising a coal liquefaction facility and a coal gasification facility.

25. The method of claim 22, wherein at least two of the first energy production technology, the second energy production technology, and the third energy production technology are located in close proximity to each other.

26. The method of claim 22, wherein the first energy production technology includes a gasifier boiler, and flare gas is introduced into the gasifier boiler.

27. The method of claim 22, wherein the second energy production technology includes a Fischer-Tropsch reactor, and hydrogen feedstock is introduced into the Fischer-Tropsch reactor.

28. The method of claim 22, Wherein the first energy production technology includes a nuclear power plant and the second energy production technology includes a plasma gasifier, and waste steam from the nuclear power plant is directed into the plasma gasifier.

29. The method of claim 28, wherein natural gas and flare gas are directed into the plasma gasifier.

30. The method of claim 22, wherein the first energy production technology is a power plant that produces electric power, the second energy production technology is a coal liquefaction facility that produces liquid fuel, and the third energy production technology is a bioreactor that produces biofuel.

31. A method of energy production, comprising:
operating an integrated energy production facility, the integrated energy production facility including at least three individual energy production facilities fluidly coupled with each other, each of the three individual energy production facilities being selected from a group consisting of a power plant, a coal to liquid fuel facility, a coal to gaseous fuel facility, and a bioreactor, each of the individual energy production facilities producing energy and emitting byproducts that include at least one of $CO_2$, an oxide of sulfur, and an oxide of nitrogen, wherein operating the integrated energy production facility includes utilizing at least a portion of the byproducts to produce the energy; and
releasing a portion of the byproducts to atmosphere, a concentration of at least one of $CO_2$, the oxide of sulfur, and the oxide of nitrogen being lower in the released portion than in a case where the individual energy production facilities are not integrated.

32. The method of claim 31, wherein operating the integrated energy production facility reduces a cost of implementation of at least one of the three individual energy production facilities as compared to the case where the three individual energy production facilities are not integrated.

33. The method of claim 32, Wherein at least two of the three individual energy production facilities are located in close proximity to each other to reduce the cost of implementation.

34. The method of claim 31, wherein releasing the portion of the byproducts to atmosphere includes electro-dynamic carbon. emission separation.

* * * * *

UNITED STATES PATENT AND TRADEMARK OFFICE
CERTIFICATE OF CORRECTION

PATENT NO. : 8,383,870 B2
APPLICATION NO. : 12/379249
DATED : February 26, 2013
INVENTOR(S) : Roy C. Knight, Rolf L. Onjukka and Patrick J. Doyle Page 1 of 1

It is certified that error appears in the above-identified patent and that said Letters Patent is hereby corrected as shown below:

In the Claims:

Claim 16, col. 16, line 45, "facility," should read as --facility.--.

Claim 28, col. 17, line 38, "Wherein" should read as --wherein--.

Claim 33, col. 18, line 33, "Wherein" should read as --wherein--.

Signed and Sealed this
Twenty-third Day of April, 2013

Teresa Stanek Rea
*Acting Director of the United States Patent and Trademark Office*